(12) United States Patent
Gupta et al.

(10) Patent No.: US 12,232,886 B2
(45) Date of Patent: Feb. 25, 2025

(54) METHOD FOR SENSING OF BIOMETRIC DATA AND USE THEREOF FOR DETERMINING EMOTIONAL STATE OF A USER

(71) Applicant: Myant Inc., Toronto (CA)

(72) Inventors: Rishabh Gupta, Toronto (CA); S. Ali Etemad, Toronto (CA); Abdul Javaid, Toronto (CA)

(73) Assignee: Myant Inc., Toronto (CA)

( * ) Notice: Subject to any disclaimer, the term of this patent is extended or adjusted under 35 U.S.C. 154(b) by 0 days.

(21) Appl. No.: 15/639,570

(22) Filed: Jun. 30, 2017

(65) Prior Publication Data

US 2019/0000384 A1  Jan. 3, 2019

(51) Int. Cl.
*A61B 5/00* (2006.01)
*A61B 5/0205* (2006.01)
(Continued)

(52) U.S. Cl.
CPC ........ *A61B 5/6804* (2013.01); *A61B 5/02055* (2013.01); *A61B 5/1118* (2013.01); *A61B 5/1123* (2013.01); *A61B 5/4538* (2013.01); *A61B 5/6831* (2013.01); *A61B 5/0537* (2013.01); *A61B 5/0816* (2013.01); *A61B 5/1116* (2013.01); *A61B 5/165* (2013.01);
(Continued)

(58) Field of Classification Search
CPC ......... A61B 5/0245; A61B 5/05; A61B 5/053; A61B 5/0531; A61B 5/0002; A61B 5/0205; A61B 5/6802; A61B 5/6804
USPC .................................. 600/301, 546
See application file for complete search history.

(56) References Cited

U.S. PATENT DOCUMENTS 6,190,314 B1  2/2001 Ark et al.
2004/0073093 A1 *  4/2004 Hatlestad .............. A61B 5/1116
600/300
(Continued)

FOREIGN PATENT DOCUMENTS

CN  101065752 B  10/2007
CN  105286853 B  2/2016
(Continued)

OTHER PUBLICATIONS

International Search Report & Written Opinion, mailed Oct. 12, 2018, in related PCT Application No. PCT/CA2018/000133.
(Continued)

*Primary Examiner* — Sana Sahand
(74) *Attorney, Agent, or Firm* — Norton Rose Fulbright Canada LLP

(57) ABSTRACT

A method of determining data model for use in predicting a state of a user based on collected biometric data collected via a sensor platform, the method comprising receiving from sensors of the sensor platform a plurality of the biometric data; extracting a plurality of representative features from the plurality of biometric data; receiving a plurality of user affect parameters associated with the plurality of representative features; correlating the plurality of user affect parameters with the plurality of representative features to determine a set of representative feature-affect pairings for the data model as a plurality of model data parameters; and storing the data model for subsequent use in determining the real time state of the user.

15 Claims, 29 Drawing Sheets

(51) Int. Cl.
*A61B 5/11* (2006.01)
*A61B 5/0537* (2021.01)
*A61B 5/08* (2006.01)
*A61B 5/16* (2006.01)

(52) U.S. Cl.
CPC ........... *A61B 5/7246* (2013.01); *A61B 5/7267* (2013.01); *A61B 5/7275* (2013.01)

(56) References Cited

U.S. PATENT DOCUMENTS

| | | | | |
|---|---|---|---|---|
| 2004/0133081 | A1* | 7/2004 | Teller | A61B 5/01 600/300 |
| 2008/0167535 | A1* | 7/2008 | Stivoric | F24F 11/30 600/301 |
| 2008/0167861 | A1 | 7/2008 | Inoue et al. | |
| 2008/0221401 | A1 | 9/2008 | Derchak et al. | |
| 2010/0286532 | A1* | 11/2010 | Farringdon | A61B 5/0428 600/483 |
| 2011/0245633 | A1 | 10/2011 | Goldberg et al. | |
| 2012/0071743 | A1* | 3/2012 | Todorov | G06F 19/3481 600/372 |
| 2012/0221310 | A1* | 8/2012 | Sarrafzadeh | A61B 5/0205 703/11 |
| 2012/0264446 | A1* | 10/2012 | Xie | G01C 22/00 455/456.1 |
| 2012/0271121 | A1* | 10/2012 | Della Torre | A61B 5/024 600/301 |
| 2013/0289889 | A1* | 10/2013 | Yuen | A61B 5/0024 702/19 |
| 2014/0007180 | A1 | 1/2014 | Agrawal et al. | |
| 2014/0031705 | A1* | 1/2014 | Kurzweil | A61B 5/0408 600/506 |
| 2014/0107531 | A1* | 4/2014 | Baldwin | G06K 9/00348 600/595 |
| 2014/0135593 | A1* | 5/2014 | Jayalth | A61B 5/0004 600/301 |
| 2014/0142485 | A1* | 5/2014 | Berry | A61B 5/1116 602/19 |
| 2014/0234815 | A1* | 8/2014 | Jang | G09B 19/00 434/236 |
| 2014/0288435 | A1* | 9/2014 | Richards | A61B 5/02427 600/479 |
| 2014/0358193 | A1* | 12/2014 | Lyons | A61N 1/37229 607/48 |
| 2015/0086949 | A1 | 3/2015 | Li et al. | |
| 2015/0182128 | A1* | 7/2015 | Magi | A61B 5/0205 340/539.12 |
| 2015/0272483 | A1* | 10/2015 | Etemad | A61B 5/05 600/409 |
| 2015/0272501 | A1* | 10/2015 | MacEachern | A61B 5/0531 600/301 |
| 2015/0327804 | A1* | 11/2015 | Lefever | A61B 5/0205 600/483 |
| 2016/0066859 | A1* | 3/2016 | Crawford | A61B 5/7264 600/301 |
| 2016/0302711 | A1 | 10/2016 | Frank et al. | |
| 2017/0011640 | A1 | 1/2017 | Rebollo-Mendez | |
| 2017/0055881 | A1* | 3/2017 | Kang | A61B 5/6823 |
| 2017/0188927 | A1 | 7/2017 | Nakashima et al. | |
| 2017/0265781 | A1* | 9/2017 | Larson | G16H 50/20 |
| 2018/0325440 | A1* | 11/2018 | Wang | A61B 5/0205 |
| 2019/0051133 | A1* | 2/2019 | Poupyrev | A61B 5/1116 |
| 2019/0150820 | A1* | 5/2019 | Lee | A61B 5/7475 |

FOREIGN PATENT DOCUMENTS

| | | |
|---|---|---|
| CN | 105827731 A | 8/2016 |
| JP | 2005058534 A | 3/2005 |
| WO | 2015182077 A1 | 12/2015 |
| WO | 2017046669 A1 | 3/2017 |

OTHER PUBLICATIONS

Lee et al., "Using neural network to recognize human emotions from heart rate variability and skin resistance," Proceedings of the 2005 IEEE Engineering in Medicine and Biology 27th Annual Conference Shanghai China, Sep. 1-4, 2005, vol. 4, pp. 5523-5525, [online], retrieved on Oct. 9, 2018, retrieved from the internet: <https://ieeexplore.ieee.org/abstract/document/1615734/>.
Lisetti et al., "Using noninvasive wearable computers to recognize human emotions from physiological signals," EURASIP journal on applied signal processing, 2004, pp. 1672-1987, [online], retrieved on Oct. 9, 2018, retrieved from the internet: <https://dl.acm.org/citation.cfm?id=1289480>.
EPO, European Supplementary Search Report for EP Application No. 18824848.8 Jun. 16, 2021.
JPO, Office Action for JP Application No. 2019-572360 dated Apr. 5, 2022.
CNIPA, Search Report and Office Action dated Mar. 16, 2023 received in Chinese Patent Application No. 201880043280.0.
Office Action dated Dec. 8, 2023 issued by Chinese Patent Office in connection with Chinese Application No. 201880043280.
Office Action from European Patent Office in connection with EP 18824848.8 dated May 22, 2024.
JPO, Office Action dated Nov. 8, 2022 received in Japanese application No. 2019-572360.

* cited by examiner

Improve your State of Mind

Detect what makes you stressed, and use our app to get you back into the right state of mind. SKIIN's smart notiifcations can remind you to breathe after a sressful event, and cope with the things life throws at you.

43

Optimize Sleep

If you're constantly tired in the mornings, it's probably related to the efficiency of your sleep. SKIIN uses the most advanced sensors located on the waistband of the garment to accurately track your sleep. Wake up feeling refreshed.

43

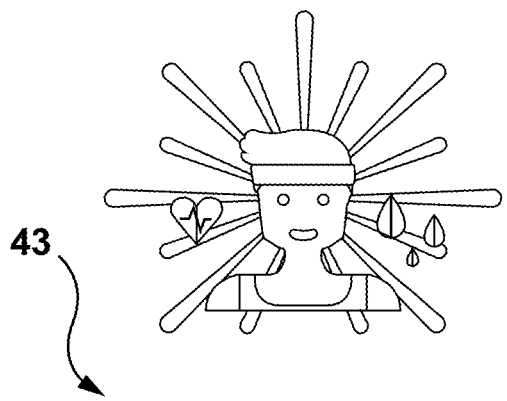

43

Be Active, Feel Better

Being active is important to your physical and mental health. SKIIN can tell you if you're spending enough time on your feet. taking enough steps, and keeping your posture upright.

43

Control your Home

Your smart home should react to you: not the other way around. Use SKIIN to control your thermostat. lights and speakers based on your mood and body temperature.

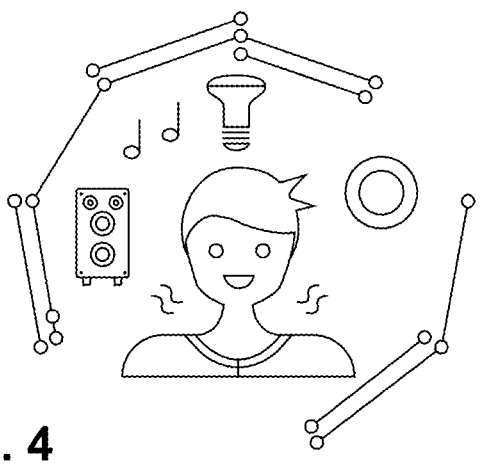

FIG. 4

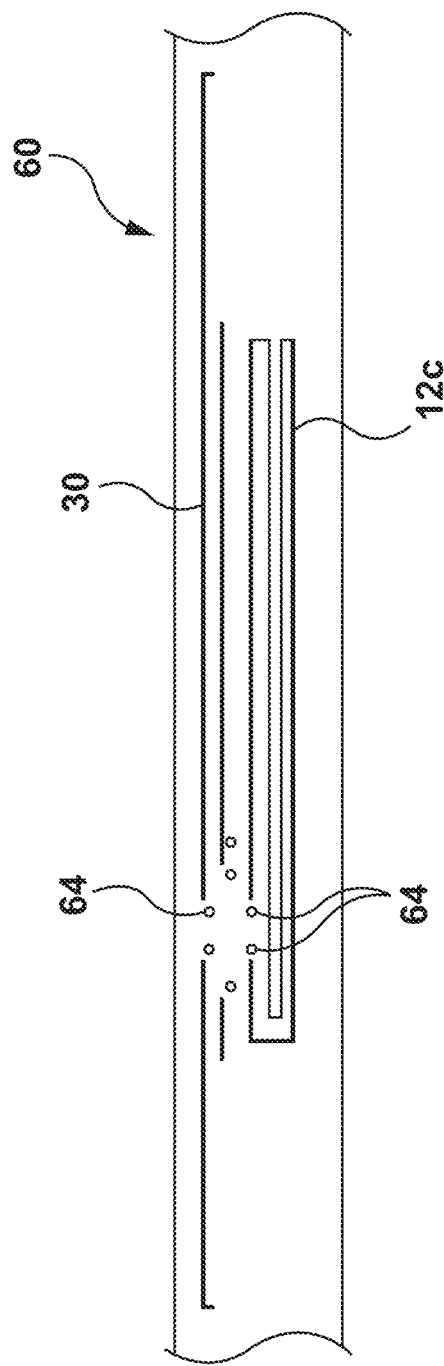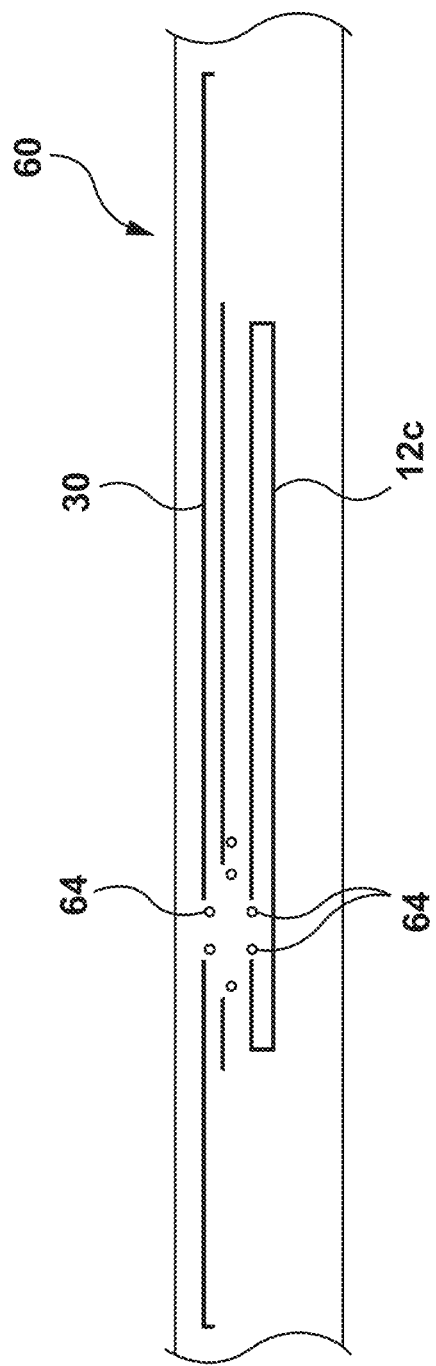

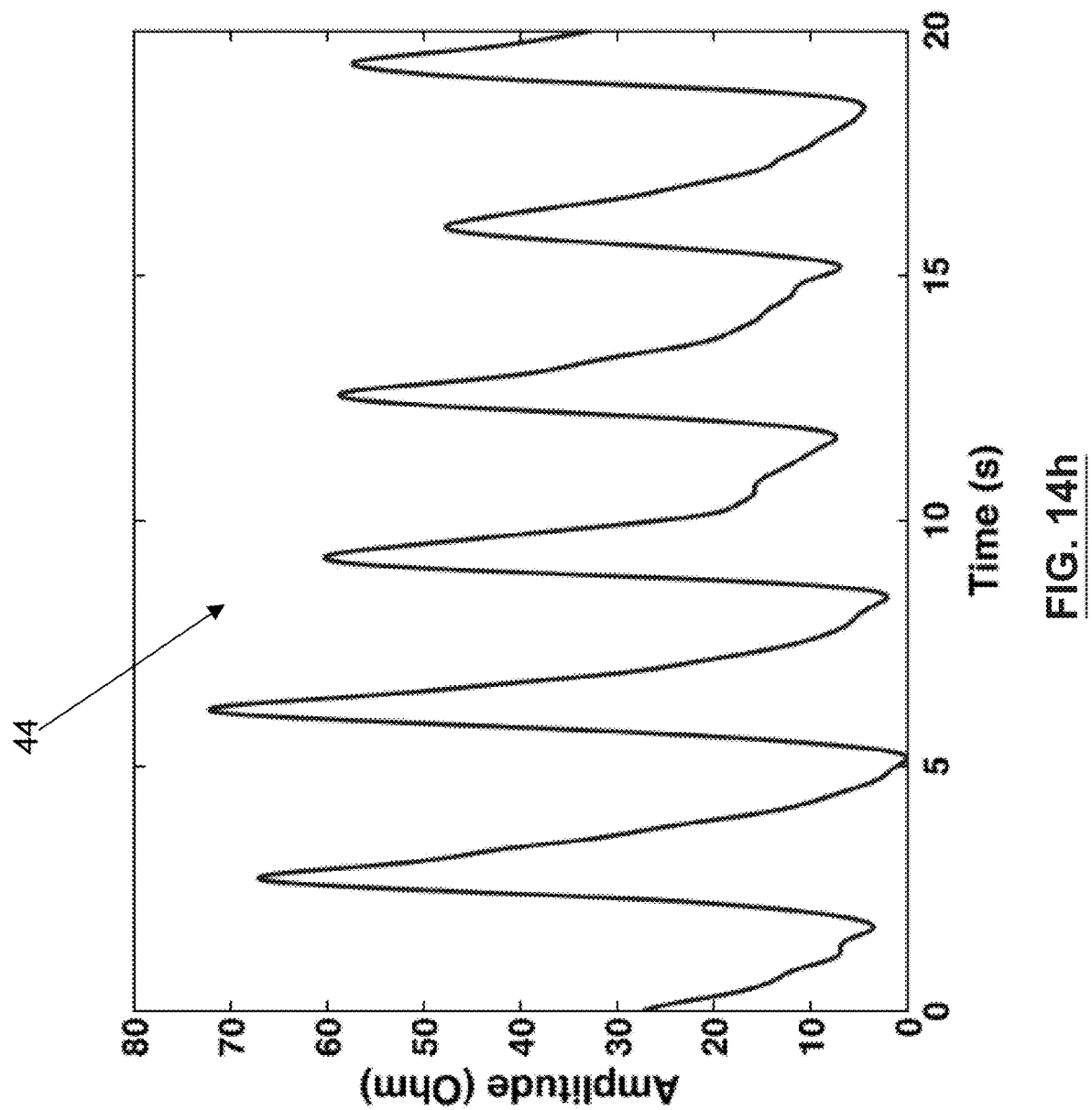

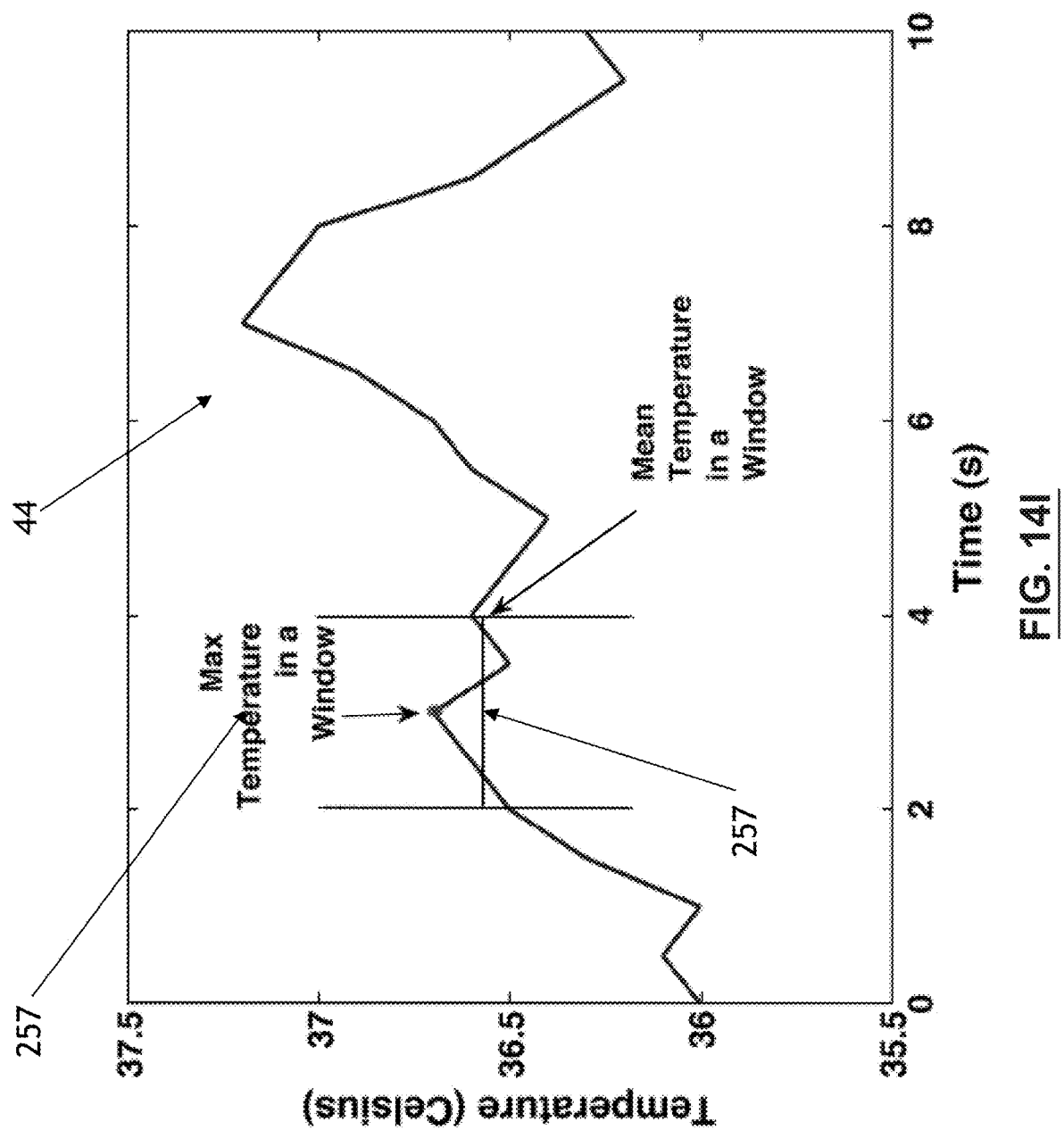

METHOD FOR SENSING OF BIOMETRIC DATA AND USE THEREOF FOR DETERMINING EMOTIONAL STATE OF A USER

FIELD

The present disclosure relates to sensing systems for biometric data.

BACKGROUND

Sensing of biometric data in today's technological based environment is key to understanding and affecting the state of a garment wearer. In particular, athletes and medical patients, among a number of other consumers, are key individuals for much needed accurate and up-to-date (i.e. real-time) biometric sensing, in order to inform (and potentially change) the wearer state (e.g. emotional state). However, state of the art sensor arrangements and methods of data processing are cumbersome and have limited applicability and adaptability to a wearer's varied lifestyle, including ever-changing physical and mental states.

SUMMARY

It is an object of the present invention to provide a sensing platform, data processing, and method of use thereof to obviate or mitigate at least one of the above presented disadvantages.

An aspect provided is a method of determining data model for use in predicting a state of a user based on collected biometric data collected via a sensor platform, the method comprising: receiving from sensors of the sensor platform a plurality of the biometric data; extracting a plurality of representative features from the plurality of biometric data; receiving a plurality of user affect parameters associated with the plurality of representative features; correlating the plurality of user affect parameters with the plurality of representative features to determine a set of representative feature-affect pairings for the data model as a plurality of model data parameters; and storing the data model for subsequent use in determining the real time state of the user.

A further aspect provided is a method of using a sensor platform of a garment of a wearer in order to determine a wearer state using a plurality of sensed biometric data and a stored data model, the method comprising: receiving from sensors the sensor platform a plurality of biometric data; determining a plurality of data features from the plurality of biometric data; comparing the plurality of data features with a set of representative feature-affect pairings of the data model, the feature-affect pairings including effects representing possible states for the wearer; selecting one or more of the possible states as a result of said comparing to provide the wearer state; and reporting the wearer state to the wearer as a presentation using a user interface of a presentation device.

BRIEF DESCRIPTION OF THE DRAWINGS

The foregoing and other aspects will now be described by way of example only with reference to the attached drawings, in which:

FIG. 4 shows example applications of the biometric data combinations;

FIGS. 8 and 9 show further embodiments of the sensors of FIG. 1;

DETAILED DESCRIPTION

Figure 1:
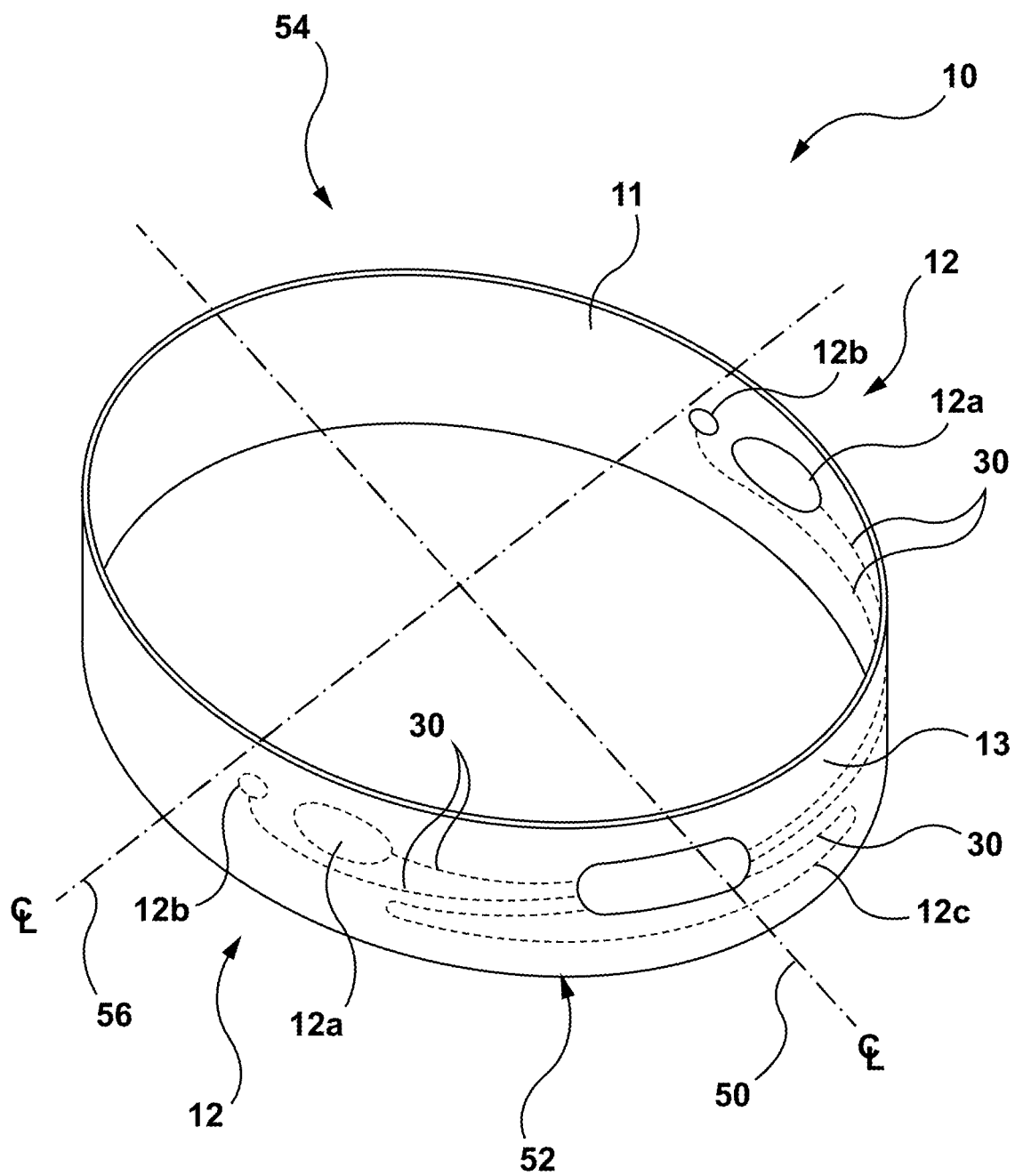
FIG. 1 is a perspective view of a band containing a plurality of sensors.
Figure 2:
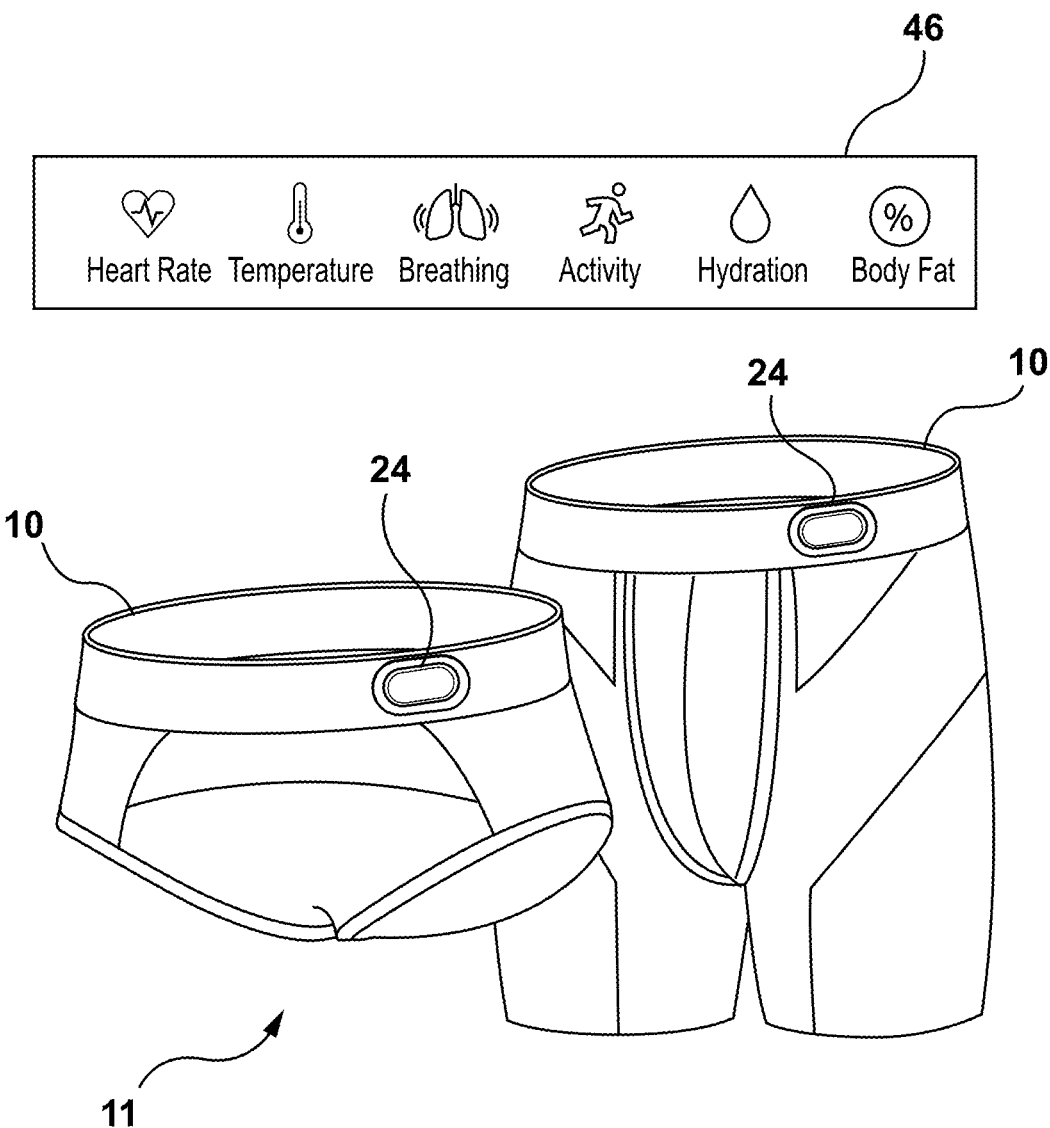
FIG. 2 is a view of the band shown in FIG. 1 incorporated into an article of clothing.

Referring to FIG. 1, shown is a fabric band 10, preferable having a resilient knit type, for fitting around a body part of a wearer (not shown), in order to collect different modes/types of biometric data based on the type/number of sensors 12 positioned either on or otherwise knit/woven (e.g. embroidered) into the fabric making up the body of the band 10. It is recognized that the body part can be such as but not limited to: waist or abdomen; limb such as a leg or arm; torso/trunk; buttocks; foot or ankle; wrist or hand; and/or head. The fabric band 10 can be provided as a stand-alone article or can be combined/combined into an article of clothing such as but not limited to: underwear 11 (see FIG. 2—such as but not limited to any type of undergarment including jockey shorts, panties, undershirts, and bras); socks, limb bands (e.g. knee band); shirt (e.g. undershirt); etc. In terms of combined into an article of clothing (i.e. garment 11), the band 10 can be formed as an integral component of the interlacing of the fibres making up the garment 11. The fabric of the body of the band 10 can be comprised of interlaced resilient fibres (e.g. stretchable natural and/or synthetic material and/or a combination of stretchable and non-stretchable materials).

Referring again to FIG. 1, provided as distributed about the band 10, e.g. mounted on an interior surface 111 (i.e. inward facing towards the body of the wearer), are a series of sensors/electrodes 12 including ECG sensors 12$a$, bio impedance sensors 12*b*, and strain gauge sensors 12*c*. It is recognized that the sensors 12 can be composed of Electroactive polymers, or EAPs, and/or woven or knit plurality of conductive fibres constructed in a sensor/electrode configuration (e.g. a patch). The sensors 12 can also include a position/location sensor in order to be able to detect the physical location of the wearer (e.g. location within or outside of their home/building).

Also positioned on the band 10, for example on an exterior surface 13 (i.e. outward facing from the wearer), is series of electrical components 15 including a computer device 14 (see FIG. 3) including a computer processor 16, a memory 18 for executing stored instructions for receiving and processing of data obtained from the sensors 12, as well as communicating via a network interface 20 with a network 22 (e.g. Wi-Fi, Bluetooth, attached wired cable, etc.) as well as sending and receiving electrical signals from the sensors 12. The processor 16, memory 18 and network interface 20 are mounted on a printed circuit board 26, which is housed in a housing 24 attached to the band 10. Also connected to the PCB 24 is a temperature sensor 12*d* for measuring a body temperature of the wearer. Also mounted in the housing is a power supply 28 (e.g. battery) for powering the various electrical components 15 within the housing 24 as well as the sensors 12*a*,*b*,*c* external to the housing 24, connected via conductive communication pathways 30 (e.g. wires—see FIG. 1—woven into the fabric weave/knit of the band 10 textile). The pathways 30 can be coupled to the sensors 12 via use of a conductive grommet, as desired. Also provided is a series of motion sensors 36 (e.g. accelerometer (s) and gyroscopes) for determining movements of the wearer, including posture as further described below. The sensors 12 can also be provided as speaker/microphone (e.g. for auditory signals/communication with the wearer), illumination sensors (e.g. LEDS—for visual signals/communication with the wearer) and haptic/vibrations sensors (e.g. actuators—for motion/touch signals./communication with the wearer).

Sensor Examples

The sensors 12 can be composed of Electroactive polymers, or EAPs, which are polymers that exhibit a change in size or shape when stimulated by an electric field. EAPS could also exhibit a change in electrical field if stimulated by mechanical deformation. The most common applications of this type of material are in actuators and sensors. A typical characteristic property of an EAP is that they will undergo deformation while sustaining forces. For example, EPDM rubber containing various additives for optimum conductivity, flexibility and ease of fabrication can be used as a sensor 12 material for measuring electrode impedance measured on human skin of the wearer. Further, EAPs may be used to measure ECG as well as measuring deformation (i.e. expansion of the waist and therefore breathing can be inferred from EAPs). ECG can be measured using surface electrodes, textile or polymer, as desired.

These electrodes 12 can be capable of recording bio potential signals such as ECG while for low-amplitude signals such as EEG, as coupled via pathways 30 with an active circuit of the electrical components 15 within the housing 24. The ECG sensors 12*a* can be used to collect and transmit signals to the computer processor 16 reflective of the heart rate of the wearer. AS such, it is recognized that the electrodes as sensors 12 can be composed of conductive yarn/fibres (e.g. knitted, woven, embroidery using conductive fibres—e.g. silver wire/threads) of the band 10, as desired.

In terms of bioelectrical impedance, these sensors 12*a*,*b* and their measurements can be used in analysis (BIA) via the processor 16 and memory 18 instructions for estimating body composition, and in particular body fat. In terms of estimating body fat, BIA actually determines the electrical impedance, or opposition to the flow of an electric current through body tissues of the wearer interposed between the sensors 12 (e.g. 12*a*,*b*), which can then be used to estimate total body water (TBW), which can be used to estimate fat-free body mass and, by difference with body weight, body fat.

In terms of strain sensing, these sensors 12*c* can be operated as a strain gauge to take advantage of the physical property of electrical conductance and its dependence on the conductor's geometry. When the electrical conductor 12*c* is stretched within the limits of its elasticity such that it does not break or permanently deform, the sensor 12*c* will become narrower and longer, changes that increase its electrical resistance end-to-end. Conversely, when the sensor 12*c* is compressed such that it does not buckle, the sensor 12*c* will broaden and shorten, changes that decrease its electrical resistance end-to-end. From the measured electrical resistance of the strain gauge, via the power 28 that is administered to the sensors 12 via the computer processor 16 acting on stored 18 instructions, the amount of induced stress can be inferred. For example, a strain gauge 12*c* arranged as a long, thin conductive fibres in a zig-zag pattern of parallel lines such that a small amount of stress in the direction of the orientation of the parallel lines results in a multiplicatively larger strain measurement over the effective length of the conductor surfaces in the array of conductive lines—and hence a multiplicatively larger change in resistance—than would be observed with a single straight-line conductive wire. In terms of location/structure of the strain gauge 12*c*, the strain gauge can be located around the circumference of the band 10. A further embodiment is where the strain gauge 12*c* is located in a portion of the circumference, for example in a serpentine arrangement, positioned in a front 52 portion (positioned adjacent to the front of the wearer) of the band 10. The strain gauge 12*c* can be configured for sensing in the k Ohm range.

In terms of temperature sensor 12*d*, this sensor is used to measure the dynamic body temperature of the wear. For example, the temperature sensor 12*d* can be a thermistor type sensor, which is a thermally sensitive resistors whose prime function is to exhibit a large, predictable and precise change in electrical resistance when subjected to a corresponding change in body temperature. Examples can include Negative Temperature Coefficient (NTC) thermistors exhibiting a decrease in electrical resistance when subjected to an increase in body temperature and Positive Temperature Coefficient (PTC) thermistors exhibiting an increase in electrical resistance when subjected to an increase in body temperature. Other temperature sensor types can include thermocouples, resistance thermometers and/or silicon bandgap temperature sensors as desired. It is also recognized that the sensors 12 can include haptic feedback sensors that can be actuated via the computer processor 16 in response to sensed data 44 processed onboard by the processor 16 and/or instructions received from a third party device 60 or the wearer (operator of the computer device 40) via an interface 20. Another example of temperature sensors 12*d* is where thermocouples could be knitted into the band 10 fabric using textile and coupled directly to the body of the wearer through close proximity/contact in order to get more accurate temperature readings.

Sensed Data and Processing

Referring again to FIGS. 2 and 3, the processor 16 (acting on stored 18 instructions) can transmit the collected data 44 (in raw format and/or in preprocessed format from the sensors 12) to an external computer device 40 (e.g. smartphone or other desktop application) for viewing and/or further processing of the sense data. For example, the device 40 application can display the sensed data 44 in a dashboard type format 46 on a display 42 (or other type of GUI interface) for viewing by the wearer (or by another person other than the wearer that has been provided access to the data 44). For example, the sensed data 44 can be provided in a dashboard format indicating real-time (or other selected dynamic periodic frequency) of: body temperature for indicating fluctuations in skin temperature; gyroscope/accelerometer measurements for indicating amount/degree of physical activity (i.e. via sensed motion) of the wearer as well as contributing via gyroscope readings of wearer posture (for example in the case where the band 10 is positioned at the waist of the wearer) as well as determined calculation of number of calories expended; strain gauge measurements (e.g. via conductive yarn) in order to indicate real-time breathing of the wearer as the band 10 expands and contracts as well as the ability to differentiate strain degree contributing to posture angle (i.e. band and associated strain sensor 12c with change in length as the posture of the wearer changes due to bending at the waist—in the case of the underwear 11 example of FIG. 2); real-time heart rate measurements based on sensed ECG data using the sensors 12a; and real-time hydration/body fat measurements based on galvanic sensing using the sensors 12b (and optionally 12a as further described below).

It is recognized that multiple sources of sensed data (e.g. temperature sensor 12d with activity/motion sensors 36 can be used in an algorithm stored in memory 18 to calculate calories expended based on activity combined with body temperature). Other combinations of sensed data types can include combinations such as but not limited to: heart rate with activity data; heart rate with activity data with temperature; activity data with bio impedance data; strain gauge for breathing rate data determination with activity data and heart rate data for determination of exertion levels; etc. It is also realized that combinations of sensor type readings can be used by the computer processor 16 to determine exercise activity type being performed by the wearer, based on computer models of activity type with typical sensor data, for example gradual changes in body posture with detected lower levels of heart rate and breathing could be indicative of a wearer practicing yoga. A further type of multiple sensed data usage can be for accelerometer and gyroscope data, such that both can be used or one can be used and the other discounted during determination of a selected metric of the dashboard 46. For example, in the case of the band 10 being situated at the waist of an overweight person, the "off-vertical" reading of the gyroscope would not be indicative of a bent posture (from the vertical), rather due to the folded waistband due to body composition. As such, the degree of gyroscope readings would be discounted from the calculation of the posture determination.

Referring again to FIG. 1, the location of the sensors 12 a,b are such that they are positioned in pairs on either side of a centerline 50, in order to position an appropriate amount of body mass between the sensors 12a,b as well as providing an appropriate conductive path through the body of the wearer (e.g. cross body measurement). It is also recognized that placement of the sensors 12a,b are preferred in body regions where muscle noise (actions of muscles can introduce signal noise into the adjacent sensors 12) is minimized. As such, the sensors 12a,b can be positioned in the band 10 in a location for positioning adjacent to the hip and/or the kidney of the wearer in the case where the band 10 is positioned at the waist. It is recognized that positioning the sensors 12a,b in the band 10 in order to be adjacent to either hip of the wearer, i.e. both sensors 12a,b of the pair to one side of the centerline 56 of the band 10, would provide for a lower signal amplitude/quality when wearer activity is subdued (e.g. resting) however would also advantageously provide an increases signal quality when the wearer is active (as the presence of utilized muscle mass adjacent to the hip region is minimal as compared to other regions about the waist).

It is also recognized that location of the sensors 12a,b can be positioned to either side of the centerline 50 running front to back rather than to either side of the centerline 56 running side to side (of the wearer), as the separation distance for the typical wearer is greater side to side rather than front to back (i.e. wider between hips verses between spine and belly button).

Further, one example option for the sensor configuration is a 4-electrode ECG sensor configuration. Cost of such an ECG design can be a factors however the design could potentially give better signal performance. The theory behind the four sensor ECG design is that the processor 16 can switch between each sensor pair (of the multiple pair ECG sensor configuration) to find the one with the best signal quality and use that one during sensed movement of the wearer.

Referring again to FIG. 3, the processor 16 and associated stored 18 instructions can be used to determine (based on received sensor 12 readings) bio impedance values by utilizing both of the ECG sensors 12a and the sensors 12b at the same time. This is advantageous as EGC sensing (using sensors 12a) cannot occur at the same time as bio impedance sensing (using sensors 12b), as signal amplitude generated by the sensors 12b oversaturates the EGC sensors 12a. As such, it is recognized that the processor 16 cycles between ECG readings and bio impedance readings (i.e. these readings are done sequentially rather than in parallel). As such, the processor instructs power to both the sensors 12a,b on one side of the centerline 50 as drivers and both the sensors 12a,b on the other side of the centerline 50 as collectors during taking of bio impedance readings. As such, it is recognized that the positioning of the sensor pair 12a and the sensor pair 12b can be symmetrical about the centerline(s) 50,56.

Figure 3:
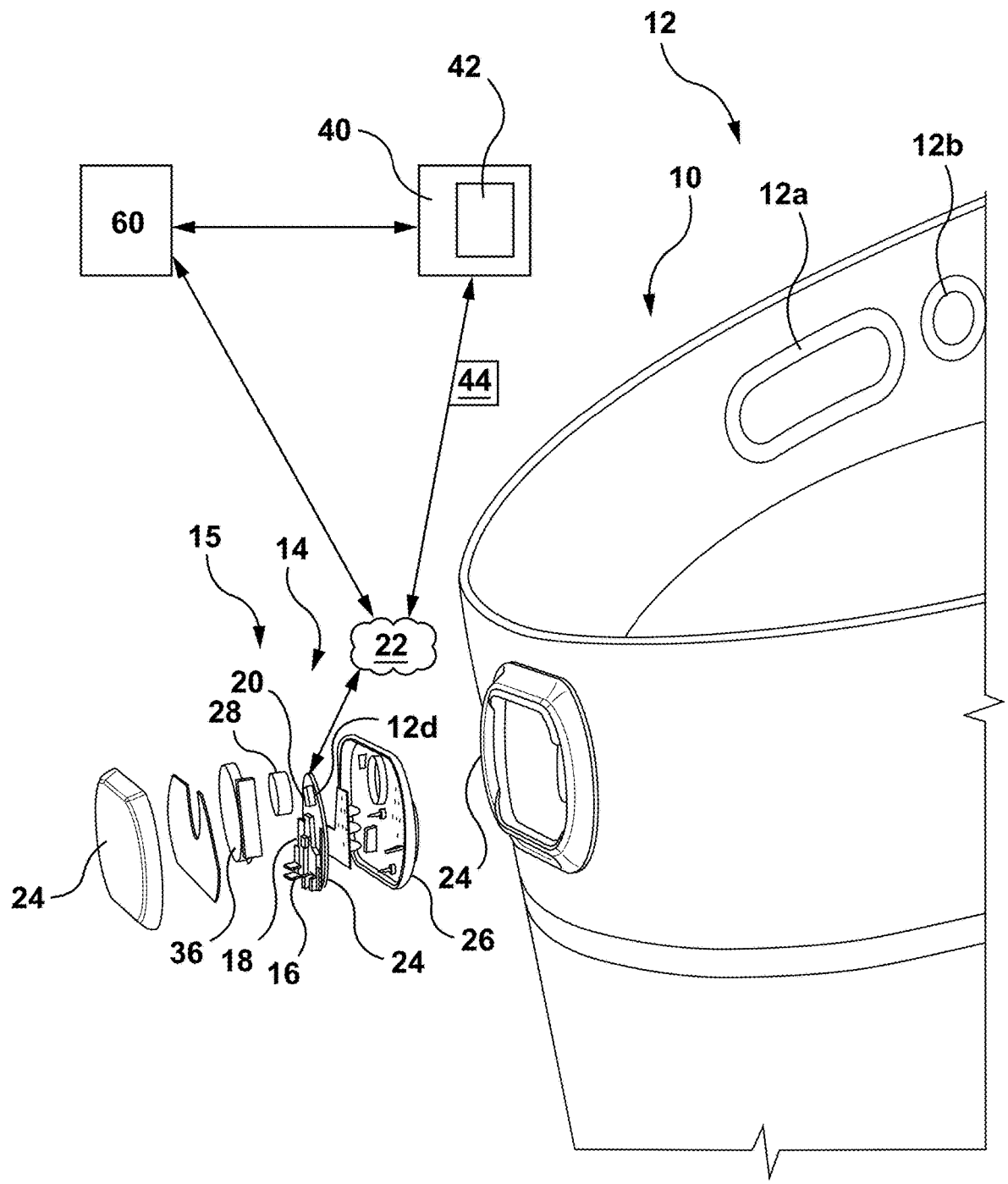
FIG. 3 shows an embodiment of the band shown in FIG. 1 with associated electrical components.

Referring to FIGS. 3 and 4, the computer device 14 can be used to send the sensed data 44 to the off band computer device 40, which can then use its own customized applications 43 to process the sensed data 44 to inform the wearer of their physical/mental state on potential adaptations/changes that can be actively done by the wearer. For example, the application 43 can report sensed data 44 pertaining to a combination of temperature and activity over time as an indicator of the quality of sleep of the wearer. Further, the application 43 can notify the wearer of a determined emotional state of the wearer (e.g. based on a combination of breathing data and ECG data, with optional activity data) as well as continued monitoring of the data combination to inform the wearer whether steps taken by the wearer are positively influencing the determined emotional state. Further, the application 43 can track and report on the degree as well as quality/nature of the wearer's activity, for example based on a combination of strain gauge data and activity data. Further, the application can interact with other external computer networked devices 60 (see FIG. 3) such as but not limited to home entertainment systems, music systems, heating system, lighting systems, etc. in response to a determined mood and/or temperature of the wearer based on a combination of sensed data (e.g. activity, heartrate, etc.).

Figure 5:
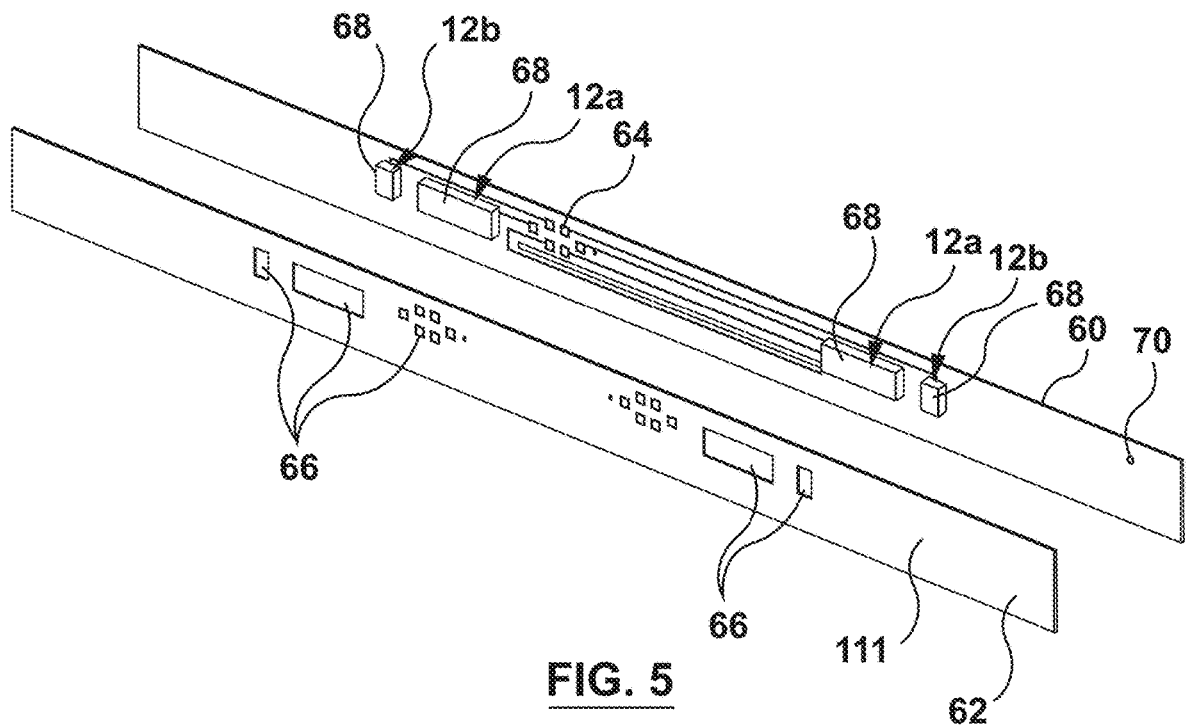
FIG. 5 shows a front perspective view of a further embodiment of the band of FIG. 1.
Figure 6:
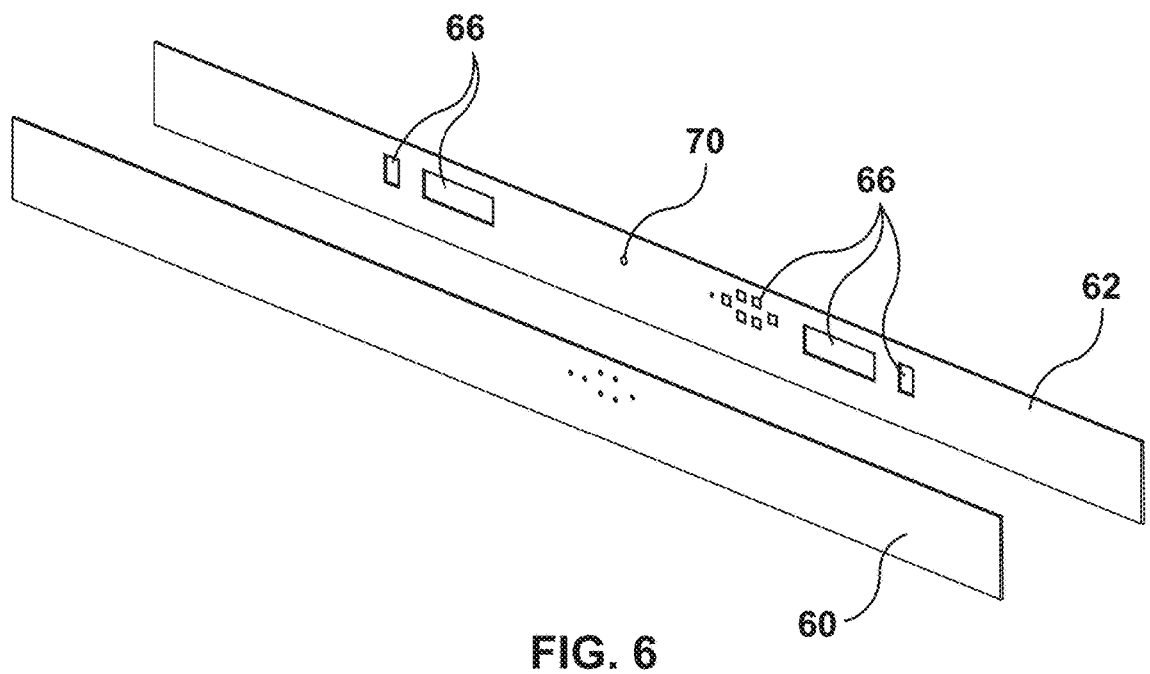
FIG. 6 shows a rear perspective view of the further embodiment of FIG. 5.

Referring to FIGS. 5 and 6, shown is an alternative embodiment of the band 10, in exploded view. In particular, the band 10 is composed of a front band portion 60 and a back band portion 62, such that the portion 60 has sensors 12a,b with communication pathways 30 electrically connecting the sensors 12a,b to respective connectors 64 (which connect to respective connector portions of the PCB 26 (see FIG. 3), in order to electrically couple the sensors 12a,b to the network interface 20). The band portion 62 has cutouts 66 in order for the sensors 12a,b to be received in the cutouts 66 when the band portions 60,62 are assembled with one another (e.g. coupled together for example by stitching via adjacently places surfaces 70), thus providing for surfaces 68 of the sensors 12a,b to become in contact with the skin of the wearer, as the surface 111 is for contact with the skin. It is recognized that the electrically conductive pathways 30 can be electrically conductive fibres interlaced with electrically insulative fibres comprising the material of the band portion 60.

Figure 7:
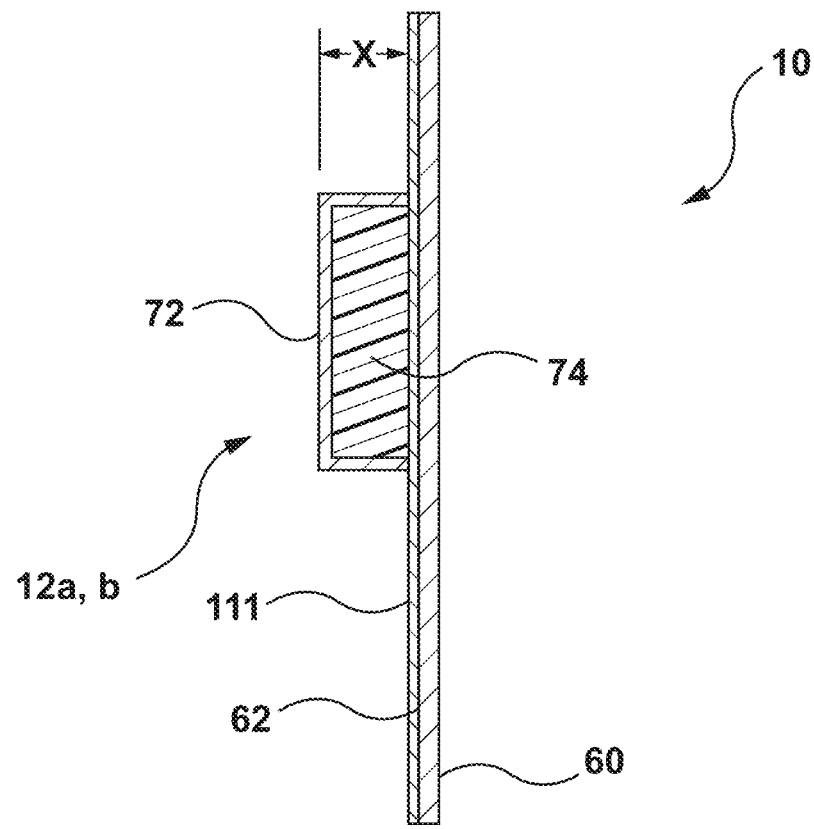
FIG. 7 shows a side view of the sensors mounted on the band of FIG. 5.

Referring to FIG. 7, shown is an example side view of one of the sensors 12a,b, such that the portions 60,62 are assembled and the sensors 12a,b are received in the cutouts 66 (see FIGS. 5,6). It is important to note that the sensors 12a,b themselves extend from the skin contact surface 111 by a distance X, thus providing for improved contact with the skin of the wearer. In particular, the sensors 12a,b can have a conductive portion 72 of the surface 68 (i.e. coupled to the communication pathways 30 extending through backing material 74) as well as the raised backing material 74 to provide for the respective extension of the conductive portion 72 of the sensors 12a,b from the surface 111. For example, the backing material 74 can be comprised of electrically insulative interlaced fibres interleaved with the textile fibres incorporating the material (i.e. electrically insulative fibres) of the band portion 62.

Referring to FIG. 8, shown is a further embodiment of the band portion 60 showing the strain gauge sensor 12c woven/knit in a serpentine fashion with other insulative fibres comprising the material of the band portion 60. As such, as shown in FIG. 7, it is recognized that once assembled, the band portion 62 would cover the strain gauge sensor 12c and thus insulate the skin of the wearer from direct contact with the electrically conductive fibres of the strain sensor 12c. FIG. 9 shows a further geometrical configuration of the strain sensor 12c.

Referring to FIGS. 5 to 8, it is recognized that they contain example geometrical layouts of the communication pathways 30 (e.g. traces) and the strain sensor 12c itself. The shown construction of the sensors 12a,b,c and band portions 60,62 are advantageous, as the entire pattern (of pathways 30 and sensor(s) 12c) is actually contained within covering portions 60,62 as one assembled (e.g. interlaced) layer of fabric, however the traces (of pathways 30 and sensor(s) 12c) are knitting inside the knit pattern and therefore as a consequence of that are insulated, therefore inhibiting any necessity of external insulation (glues, laminates, etc.). In order to inhibit undesirably application of electrical charge from the traces to the skin of the wearer. Further, the 3D shape (e.g. extension from the surface 111) of the sensors 12a,b themselves can improves the sensors 12a,b contact with the skin and can provide for the collection of biometric data across a variety of skin conditions, dry or wet.

New "IOT" Description

Figure 10:
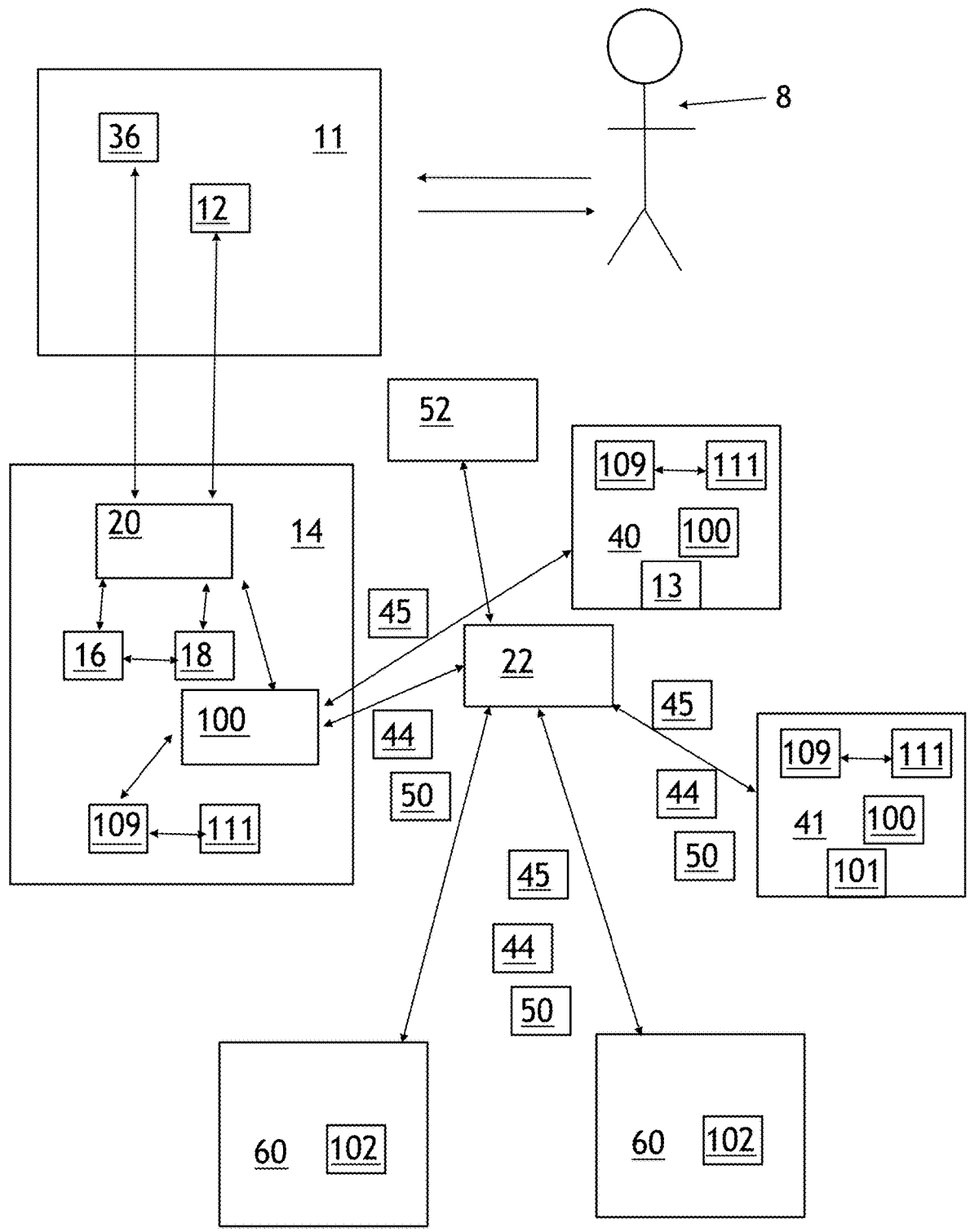
FIG. 10 shows a block diagram of a system for processing biometric data and acting thereon for the sensor platform shown in FIG. 1, by example.

Referring to FIG. 10, shown is a garment application 100 bi-directionally communicating over the network 22 with a plurality of networked devices 15, each having a device application 102 capable of sending and receiving data 44,45 (i.e. bidirectional) with the garment application 100 via the network 22. It is recognized that the garment application 100 receives biometric data 44 via the interface 20 (e.g. API) and then can send the commands 45 based on the data 44 (e.g. raw or otherwise processed) to one or more networked devices 60 in order to influence the operation of the networked device 60 via the device application 102 running on the device 60. For example, the device application 102 can be a thermostat application 102 running on a home thermostat 60 and thus able to instruct the thermostat 60 to raise or lower the temperature setting controlled by the thermostat, recognizing that there are further bidirectional use cases described by example below.

The garment application 100 receives the biometric data 44 collected by the sensors 12,36 incorporated in the garment 11 (e.g. shirt, pants/shorts, vest, underclothing, hat, and/or any other garment type incorporating the sensors 12,36 as part of or external to the band 10). The garment application 100 can interact with other external computer networked devices 60 (see FIG. 10 such as but not limited to music systems devices 60, heating system devices 60, lighting system devices 60, and other devices 60 configured to interact with the wearer 8 of the garment 11 via the garment application 100. It is recognized that the garment application 100 can be one or more applications 100 running on one or more computer platforms, for example such as but not limited to the garment application 100 executing on the computer device 14, the garment application 100 executing on the external device 40 (e.g. wearer's mobile device), and/or a cloud-based garment application 100 hosted on a wearer account on a network server 41, as desired. In any event, regardless of the one or many differently hosted garment applications 100, the garment application(s) 100 is/are configured to receive the biometric data 44 collected from the sensors 12,36 by the computer processor 16, optionally process or otherwise analyze the biometric data 44, compare the data 44 (i.e. raw or processed) against one or more stored thresholds or rule sets 45 (further described below), to generate a command 45 for instructing the device application 102 to modify functional behavior(s) of the respective networked device 60, to communicate with the networked device 60 the command 45 as well as provided responses 45 to the command from the networked device 60 in response to receiving the command 45. As further described below, the command 45 can be generated by the garment application 100 in response to a determined mood and/or temperature of the wearer based on a combination of sensed data 44 (e.g. activity, heartrate, etc.).

Figure 11:
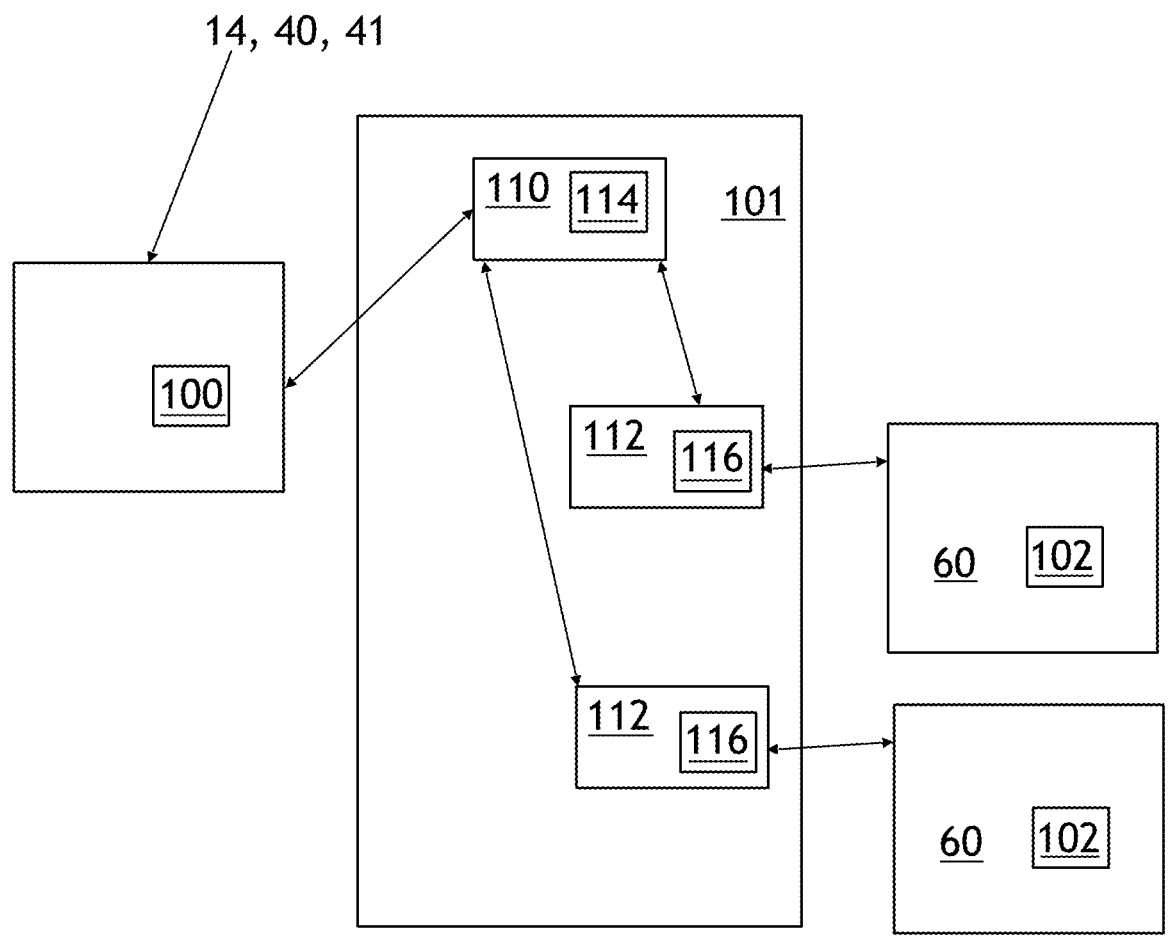
FIG. 11 is a block diagram of an interaction service for the system of FIG. 10.

Referring again to FIG. 10, a garment interaction service 101 can be implemented on the server 41, for example, however it can also be in whole or in part hosted on the external device 40, as desired. The garment interaction service 101 (see FIG. 11) contains a wearer account 110 registered with the garment application 100, as well as respective device accounts 112 registered with their respective device application 102 of their networked device 60. The accounts 110,112 are registered with the service 101 prior to network 22 interaction there-between. For example, a wearer 8 wishing to control their home thermostat 60 and their home lighting system 60 and their home music system 60 (it is recognized that one or more of these device 60 functions can be controlled by the same device application 102, as desired, rather than by separate device applications 102) can register with the interaction service 101 as well as register the network device applications 102, thus creating accounts 110,112. Using the accounts 110,112, the interaction service 101 can receive data 44, commands 45, and responses 45, thereby acting as a third party server/service for use in coordinating the network 22 interaction between the garment 11 and the device 60.

The accounts 110,112 can contain registration information such as but not limited to: wearer login and password account information, wearer settings information 114 for device 60 operation (e.g. desired device 60 operation based on wearer parameter settings), device operation settings 116 (e.g. permitted functionality accessible to modify based on received commands 45), etc. For example, in terms of wearer settings information 114, the wearer can specify music type selections (as played by music system device 60) for different wearer moods such as but not limited to "easy listening" music for active but considered happy/content wearer mood, "restful listening" music for use in calming the wearer during restful situations (e.g. sleep), "active listening" music for use in motivating the wearer to become more physically active, etc. Other settings 114 can include such as but not limited to: desired lighting levels (as moderated by lighting system device 60) based on determined wearer activity level/mental state, desired temperature settings (as moderated by heating/cooling system device 60) based on determined wearer activity level/mental state, operational mode of automobile (as moderated by automotive system device 60) based on determined wearer activity level/mental state, and/or the garment 11 itself based on functional devices 60 resident on/in the garment 11 fabric such as but not limited to actuators (e.g. electronic sensors capable of applying an electrical/vibrational stimulus to the wearer, heating device capable of applying heat to the wearer, cooling device capable of removing heat or otherwise cooling the wearer, and/or any other device 60 that can change its functional state based on receiving of the command 45 generated using sensed and processed (e.g. via application 100) biometric data 44. Another example of wearer settings information 114 is for location settings, such that the wearer can specify the definition of certain physical locations (e.g. geolocation X represents the wearer's home, geolocation Y represents the wearer's work/employment, geolocation Z represents the wearer's preferred hobby, geolocation X1 represents the wearer's location within the home—e.g. bedroom, etc.). It is also recognized that the wearer settings information 114 can be used to define the wearer's environment based on co-registration of the device 14 with an adjacent device (e.g. pairing the device with the external device 40 can be used to indicate when the wearer is exercising at their gym, driving their car, etc.). As such, it is recognized that the garment application 100 can also be informed of the wearer's activity/mental state based on information obtained from sensors/devices 13 (e.g. current Bluetooth connectivity with another device 60 such as an automotive communication system, GPS sensors resident on the external device 40, etc.).

In view of the above, it is recognized that the garment application 100 is responsible for receiving the biometric data 44 on a periodic (e.g. determined regular frequency of data 44 reporting) basis and/or on a requested basis (e.g. in response to a command 45 generated, and sent to the networked device 60 which in turn changes an operational state of the networked device 60). In this way, scheduled periodic and/or upon request, the garment application 100 can be used to monitor the physical/mental state of the wearer 8 over a period of time, and as instructed by the wearer settings 114, can adjust the operational functionality of one or more of the networked devices 60 based on received and interpreted biometric data 44.

It is recognized that the garment application 100 can have access to a plurality of data models 109 for use in comparing a plurality of biometric data 44 from two or more different sensor types (e.g. activity sensor and temperature sensor, temperature sensor and ECG sensor, activity sensor and posture sensor, activity sensor and location sensor, etc.). The data models 109 each represent a series of data 44 value combinations, which define a particular desired (or undesired) physical/mental state of the wearer 8 (for example as defined by the wearer 8). For example, data 44 can comprise; 1) a location of the home (e.g. bedroom), a time of day (e.g. nighttime), a temperature reading (e.g. elevated), and an activity reading (e.g. wearer motion), 2) can be received by the garment application 11 and 3) compared to a data model 109 representing a desired sleep pattern for the wearer 8. In the event that the data 44 matches the desired sleep pattern of the sleep data model 109, the garment application 100 would not generate any commands 45 and thereby attempt to moderate or otherwise affect any networked devices 60 (e.g. thermostat 60, music system 60, etc.) associated with the sleep data model 109.

Figure 12:
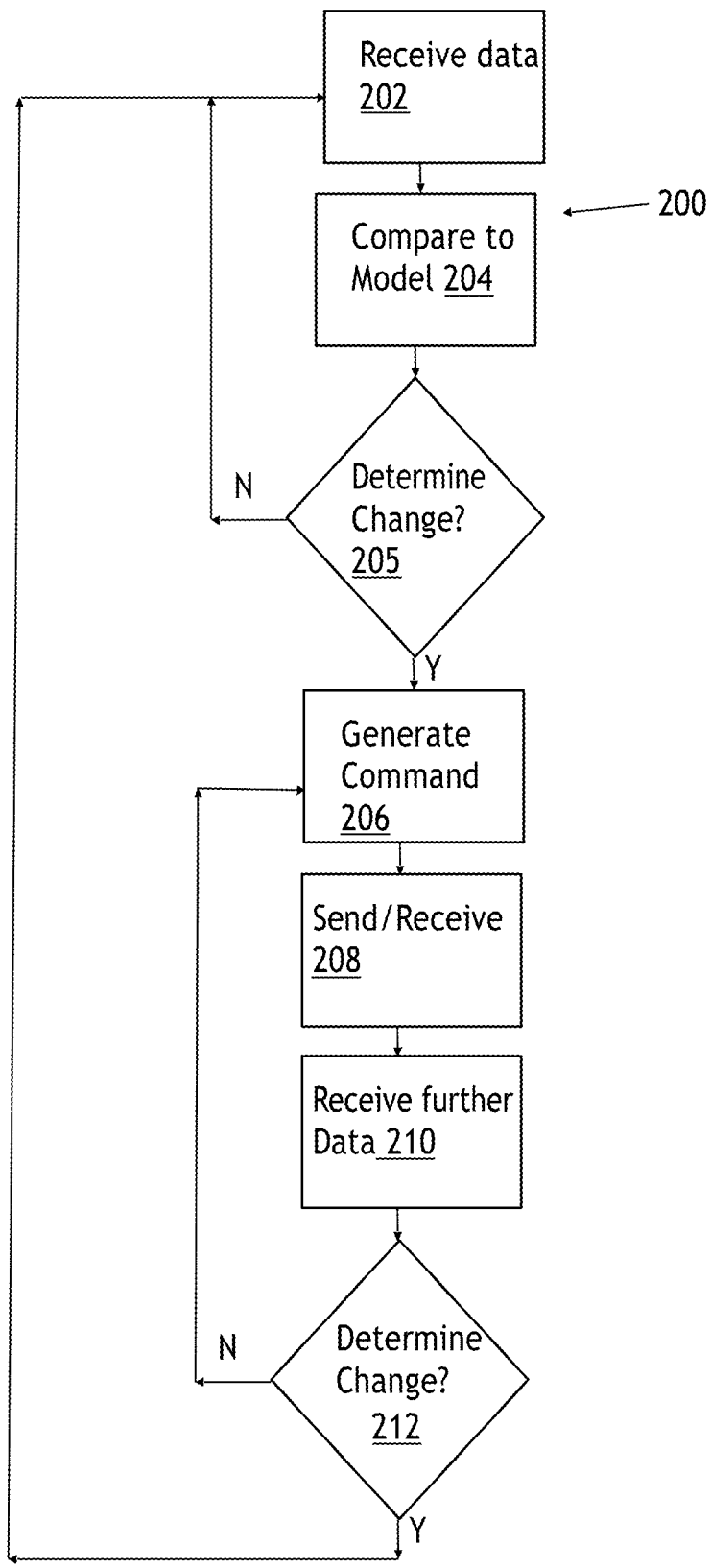
FIG. 12 is a flowchart of an example operation of the system of FIG. 10.

As such, referring to FIG. 12 for command operation 200, the garment application 100 compares 204 the biometric data 44 (as well as any other data provided by third party devices such as but not limited to the external device 40), comprising multiple data types collected/received from the sensors 12,36, to the data model(s) 109. For example, the garment application 100 can be configured to receive periodically (e.g. every 10 seconds) data 44 from each of the sensors 12,36 of the garment 11. In response to the received 202 data 44, the garment application 100 can compare 204 the data 44 to each of the model(s) 109 and generate 206 one or more commands 45 in the event the data 44 matches (or does not match) one or more of the data models 109. It is recognized that each of the data models 109 would have a set of instructions 111 (see FIG. 10) for use in determining/suggesting what action(s) is/are appropriate in the event that the data 44 matches (or does not match), and to what degree, the data patterns implicit in the data model(s) 109 match or do not match the plurality of data 44 (of different data types) provided by the sensors 12,36.

Sleep Example

One example of operation, following FIG. 12, of the garment application 100 is for monitoring 200 a sleep or restful state of the wearer 8. For example, the garment 11 by way of the sensor 12,36 data received 202 by the garment application 100 can indicate an activity level (e.g. accelerometer data 44) of the wearer 8, a temperature level (e.g. temperature sensor data 44) of the wearer 8, and a posture or body attitude level (e.g. strain sensor or gyroscopic data 44) of the wearer 8. The garment application 100 can compare 204 these received data 44 levels to one or more sleep patterns/thresholds of the sleep data model 109 in order to determine 205 if the wearer 8 is having a sleep episode that matches (e.g. representing a restful sleep) or does not match (e.g. represents a disturbed/fit full sleep) the sleep pattern(s) of the sleep data model 109. At step 206, based on the degree of match or mismatch, the garment application 100 can generate 206 a command for one or more of the networked devices 60 (as associated with the data mode 109 via the instructions 111) and send 208 the command and receive feedback 45 (e.g. an acknowledgement response, a response indicating a change or degree of change in operational function of the networked device 60, etc.) from the networked device 60. In the case of the sleep example, the garment application 100 can generate 206 a decrease temperature command 45 by a defined amount (e.g. by 2 degrees Centigrade), based on the set of rules 111, and send 208 the command 45 to the thermostat 60. The garment application 100 can receive acknowledgement 45 of the temperature decrease command from the thermostat 60 and can subsequently monitor 210 (e.g. via further programmed periodic or requested data) further data 44 of the wearer 8 to determine via a further data model 109 comparison 212 whether the new/revised data 44 (a consequence of the issued command 45) represents a desired change (e.g. improvement) 213 in the wearer's activity/mental state represented by the data model 109, or lack of improvement thereof. In the case of a desired change at step 213, the garment application 100 would refrain from issuing further commands 45 to the networked device 60 and thus continue to monitor 202 the wearer 8 via further periodic receipt of the data 44 and comparison to the data model(s) 109. If the change/no change determined at step 213 needs further commands 45 to be issued (e.g. sleep has improved but not to an acceptable level as represented in the model 109 data patterns), the garment application 100 returns to step 206.

In the above example, one potential data pattern of the sleep data model 109 is where the wearer's temperature is elevated (e.g. wearer is too hot) and the wearer's activity/motion level is also elevated (e.g. wearer is tossing and turning). The command 45 issued would be to decrease the room temperature to the thermostat and the garment application 100 would monitor the effect of the temperature change, e.g. a lowering of the wearer temperature. Subsequent monitored lowering of the wearer activity level via the new data 44 to acceptable levels as defined in the sleep data model 109 would return the garment application to operating at step 202. On the contrary, subsequent monitored raising/unchanged of the wearer activity level via the new data 44 representing non-acceptable levels as defined in the sleep data model 109 would return the garment application to operating at step 206, in an effort to continued lowering of the room temperature in order to facilitate a decrease in the wearer's body temperature and/or activity level.

Mental State Example

It is recognized that the number of potential applications for the garment 11 paired with the garment application 100 and the device application(s) 102 can be numerous. A further example is where the garment application 100 detects (i.e. via the sensed data 44) an elevated heart rate (still with acceptable norms—i.e. not indicative of a heart attack) without a corresponding increase in physical activity level. This physiological state of the wearer, as defined/matching a data model 109, could be indicative of an anxiety attack. In this case, the garment application 100 could be programmed via the instructions 111 of the data model 109 to instruct a networked device 60 such as a music system 60 to play restful/meditative music. Continued monitoring of the physical state by the garment application 100 could be used to determine by the garment application 100 if the commanded 45 changes to the operational/functional state of the networked device 60 are having any effect on the wearer's physical/mental state.

It is recognized that the data model 109 by way of the instructions and data patterns 111 can be used to define more complex state(s) of the wearer 8, via a combination of a plurality of the various sensor 12,36 types and their data. For example, the current mental state (e.g. happy, sad, anxious, excited, sedate, depressed, relaxed, etc.) can be determined as a result of a combination of the plurality of sensed data 44 matching (or not matching) the data model(s) 109 representing that mental state. For example, the data 44 for heart rate, breathing rate, temperature, activity level, and posture can be used, as a combination, to define and predict the current mental state of the wearer 8, based on the mental state modelling as represented by a mental state data model 109.

Notification Emergency Example

It is also recognized that in the event that the operation 200, as shown in FIG. 12, does not mitigate or otherwise obviate the determined match/mismatch of the data model(s) 109 performed by the garment application 100 using the sensed data 44 (i.e. as determined via the comparisons with the data model 109), the garment application 100 could be programmed via the settings 114 to send a notification 50 to a specified device 52 indicating a potential emergency/crisis event. For example, this specified device 50 could be that of a family member, medical practitioner, notification service, or friend, which would receive the notification 52 and could be informed of the wearer's activity/mental state and/or otherwise encouraged to perform some action (e.g. contact the wearer 8, contact a medical practitioner, etc.)—see FIG. 10. The device 52 could also be the external device 40 of the wearer 8, thus providing the wearer 8 with direct indication of their situation (e.g. "you are too excited and maybe you need to calm down?").

It is also recognized that the operation 200 could be used to determine an actual considered detrimental/emergency condition of the wearer 8, e.g. heart attack, car accident or other body trauma, kidnapping, etc., such that the data models 109 are used to indicate/determine (by the garment application 100 comparing the data 44 to the rules and data patterns 111 of the data model 109) that the data 44 is well outside (or inside) expected norms/thresholds defined in the data models 109. For example, the data 44 when compared to the data models 109 could indicate a heart attack (e.g. via ECG readings 44 and activity readings 44), a stroke (e.g. EGC readings 44 and activity level readings 44), kidnapping (e.g. anxiety level readings 44, activity level readings 44 and location/change in location readings 44), etc.

Mental/Physical Activity Example

A further example operation 200 can be for a planned physical activity (e.g. cycling, jogging) of the individual wearer 8. The data model 109 representing the physical activity can be used by the garment application 100 to monitor the wearer's biometric data 44, and to report to the wearer 8 via the computer device 14 (e.g. sound, light or other haptic commands/sensations) and/or via the external device 40 (e.g. sound and/or messages on a screen of the device 40) suggestions to the wearer 8 while performing the activity. For example, hydration levels (e.g. physical state) of the wearer 8 can be monitored by the garment application 100, via the sensed data 44 and comparison to the data model(s) 109 representing the activity, and thus a notification (e.g. command 45) can be sent to the wearer 8 (i.e. via the device 14,40) indicating that hydration levels are outside of a threshold (e.g. too low) and thus the wearer 8 should correct (e.g. hydrate by drinking). Again, as per the operation 200 described above, the dynamic physical state of the wearer 8 would be continually monitored by the garment application 100 (in comparison of data 44 with the data model 109) and thus further suggestions (e.g. of hydration) would be sent to the wearer 8. Alternatively, a notification 45 of the detected physical state (e.g. hydration) back within accepted norms could be sent to the wearer 8 as a consequence of the continued monitoring.

A further example operation 200 can be for a planned physical activity (e.g. cycling, jogging) of the individual wearer 8. The data model 109 representing the mental activity/state can be used by the garment application 100 to monitor the wearer's biometric data 44, and to report to the wearer 8 via the computer device 14 (e.g. sound, light or other haptic commands/sensations) and/or via the external device 40 (e.g. sound and/or messages on a screen of the device 40) suggestions to the wearer 8 while performing the activity. For example, focus levels (e.g. mental state) of the wearer 8 can be monitored by the garment application 100, via the sensed data 44 and comparison to the data model(s) 109 representing the activity (for example as a result of monitored body posture, breathing rate, heart rate, etc.), and thus a notification (e.g. command 45) can be sent to the wearer 8 (i.e. via the device 14,40) indicating that focus levels are outside of a threshold (e.g. too low) and thus the wearer 8 should correct (e.g. refocus). Again, as per the operation 200 described above, the dynamic mental state of the wearer 8 would be continually monitored by the garment application 100 (in comparison of data 44 with the data model 109) and thus further suggestions (e.g. of refocus) 45 would be sent to the wearer 8. Alternatively, a notification 45 of the detected mental state (e.g. focus) back within accepted norms could be sent to the wearer 8 as a consequence of the continued monitoring.

It is also recognized that the data model(s) 109 could be used to detect the type of physical activity being performed by the wearer 8 (e.g. yoga, cycling, etc.), based on the sensed data 44 matching a particular activity type pattern. Once detected, the garment application 100 could select and use an appropriate data model 109 representative of the detected activity type to monitor the state (e.g. physical/mental) of the wearer 8 as the activity is being performed. The physical activity can be an activity such as but not limited to: vigorous physical activity such as a physical sport (e.g. cycling, running, weight training, etc.) non-vigorous physical activity/sport (e.g. dart throwing, yoga, tai chi, etc.); active/concentrated mental activity such as computer work at the wearer's place of employment; relaxed mental activity such as reading/relaxation/listening to music/meditation; etc. In any event, it is recognized that the data models 109 can be used to optionally detect and to also monitor the physical/mental activity of the wearer 8, based on the sensed data 44 in comparison to the requisite data model(s) 109 as discussed above with respect to the operation 200.

User Affect Example

It is recognized that the number of potential applications for the garment 11 paired with the garment application 100 and the device application(s) 102 can be numerous. A further example is where the garment application 100 detects (i.e. via the sensed data 44) an elevated heart rate (still with acceptable norms—i.e. not indicative of a heart attack) without a corresponding increase in physical activity level. This physiological state of the wearer 8, as defined/matching a data model 109, could be indicative of an anxiety attack. In this case, the garment application 100 could be programmed via the instructions 111 of the data model 109 to instruct a networked device 60 such as a music system 60 to play restful/meditative music. Continued monitoring of the physiological state by the garment application 100, via the data 44 collected by the sensors 12,36, could be used to determine by the garment application 100 if the commanded changes to the operational/functional state of the networked device 60 are having any effect on the wearer's physical/mental state.

It is recognized that the data model 109 by way of the instructions and data patterns 111 can be used to define more complex state(s) of the wearer 8, via a combination of a plurality of the various sensor 12,36 types and their data. For example, the current mental state (e.g. happy, sad, anxious, excited, sedate, depressed, relaxed, etc.) can be determined as a result of a combination of the plurality of sensed data 44 matching (or not matching) the data model(s) 109 representing that mental state. For example, the data 44 for heart rate, breathing rate, temperature, activity level, and posture can be used, as a combination, to define and predict the current mental state of the wearer 8, based on the mental state modelling as represented by a mental state data model 109.

Figure 13:
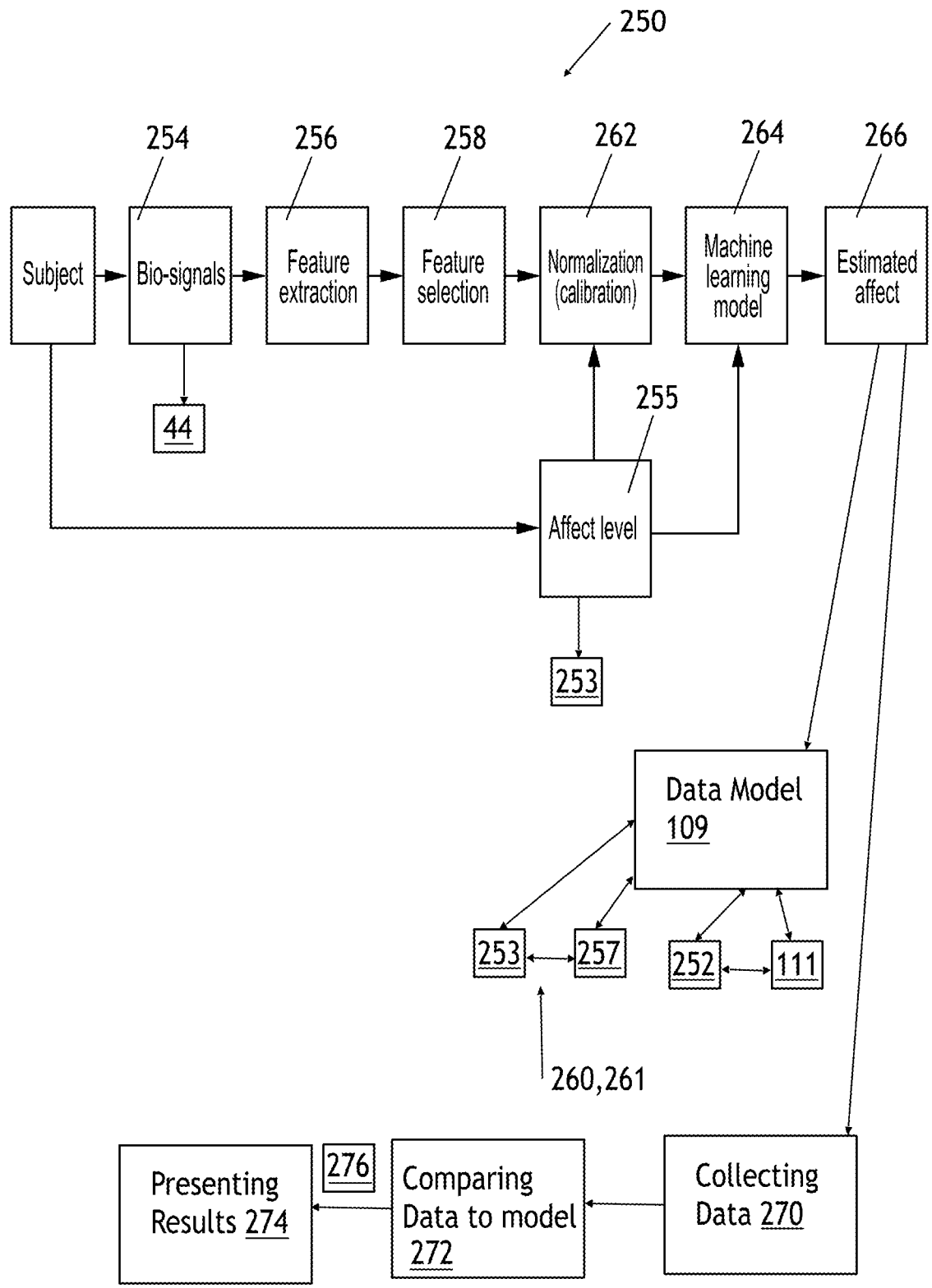
FIG. 13 is a flowchart of an example operation for generating and applying a data model for the system of FIG. 10.

Referring to FIG. 13, shown is a flowchart 250 on creation of a user affect data model 109, such that the user affect data model 109 reflects an emotional state of the wearer 8 correlated to a number of bio signal parameters 252, such as but not limited to: a dataset of biological signals 44 collected 254 via the sensors 12,36 including ECG, motion, breathing, temperature, and bio-impedance parameters 252. It is recognized that the data 44 representative of each of the parameters 252 can be provided as single mode data (i.e. temperature, ECG) and/or as combination mode data (e.g. posture, breathing—which can incorporate a combination of two or more data types such as but not limited to strain data, accelerometer data and/or gyroscopic data).

Referring again to FIG. 13, implementation of the method 250, the data 44 is collected 254 in combination with associated subject-reported affect levels (for example "stress" levels or other quantitative/qualitative emotional levels 253 as reported 255 by/of the wearer 8, for example "based on a scale of 1 to 10 what level of "stress", "happiness", etc. are you experiencing at this moment?"). The reported affect (aka, emotional level 253) can be solicited or unsolicited and entered periodically or based on certain stimuli events taking place (e.g. physical/emotional stimuli provided to the wearer 8 such as but not limited to an interactive multimedia session—such as a game, a series of pictures, a series of questions, etc.) during the collection 254 and reporting 255. At step 256, a plurality of linear and/or nonlinear features 257 in time and frequency domains (see FIGS. 14*a,b,c,d,e* by example) are extracted 256 from windows of the bio-signals 44. Each of the features 257, as singles and/or combinations, are associated with the emotional level data 253 and sent for correlation analysis 258. The correlation analysis 258 can be performed using a data processing system 300 (see FIG. 15) utilizing programmed analysis instructions such as but not limited to: Spearman rank correlations or other types of correlation analysis between features 257 and reported affect levels 253 in order to select or otherwise determine a subset of feature/affect level(s) correlations 260 that are considered representative of the affect levels 253. As such, the data model 109 contains a plurality of correlations 260 between identified features 257 and reported affect levels 253.

At step 264, one or more linear and/or nonlinear machine learning methods (e.g. such as logistic regression, neural networks, naïve Bayes, or hidden Markov models among others) is/are used to learn (i.e. determine) the relationship(s) 261 between the selected features 257 and user affect levels 253. The data model 109 can also incorporate information such as age, gender, prior mental states, and other considered as prior information. A "normalizing state" (e.g. calibration) of the user (for the particular class of affect in question) can be optionally recorded 262, where the bio-signals 44 in this state can be used to normalize the data 44 for that user in the future. This normalizing state can be measured 262 by subjecting the user to a "neutral" state (e.g. based on selected event stimuli level(s) considered as neutral or baseline administered to the user during collection 254, 255 of the data 44) or by averaging the recorded state (of the collection 254,255 of the data 44) over a selected period of time (for example one day). Alternatively/optionally, instead of or in addition to subject-reported affect levels 253, subjects can be subjected to two or more considered extreme or representative cases (e.g. calm/stress, happy/sad, etc.) of user stimuli, for example a stimuli session of (e.g. very) calm and a stimuli session of (e.g. very) stressed. In this case, an analysis model (as a set of analysis instructions) such as linear regression, logistic regression, decision trees, random forests, support vector machines, k-nearest neighbors, and/or other can be used 264 to estimate the levels in between the pair of extreme cases, for example as probability estimations. At step 266, the emotional (e.g. mental) state data model 109 is generated using the parameters 252, data 44, features 257, levels 253, correlations 260, and/or relationships 261. The data model 109 is then stored in memory of the data processing system 300 for subsequent use in reporting/estimating the emotional state of the wearer 8 by collecting 270 (e.g. in real time) the data 44 (while the wearer 8 is wearing the garment 11 and going about their daily, regular activities), analyzing 272 the collected data 44 at step 272 using the generated data model 109 (e.g. comparing the collected data 44 by feature 257 extraction of the real time data 44 collected at step 270, determining similar feature sets 260 and any related relationships 261 per the above requisite steps used during processing of the collected data 44 of step 254, and then matching the determined real-time feature sets 260 to those stored in the data model 109) in order to determine 274 the generated real time mental state 276 of the wearer 8 and present 274 to the wearer 8 on a user interface of the device 14 and/or device 40 (see FIG. 3).

As discussed above with respect to the process 200, the determined data model 109 of step 266 can be utilized to generate the commands 45 for functional applications 102 executing on one or more devices 40,41, 60, as well as to monitor at step 210 the wearer 8 as a result of command 45 execution by the application(s) 102.

Figure 14A:
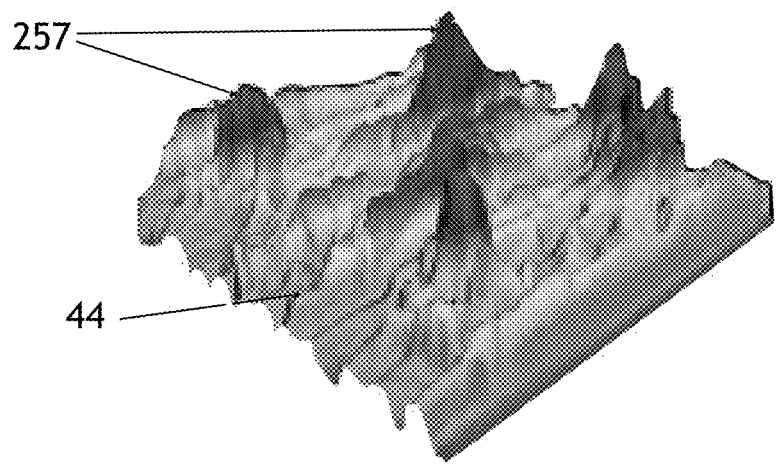
FIGS. 14$a,b,c,d,e,f,g,h,I,j,k,l$ are example embodiments of the biometric data collected by the garment of FIG. 1.

Referring to FIG. 14a, shown is a representative output of the data collection 254,270 (see FIG. 12) and resulting feature 257 representation of the data 44 (e.g. features 257 shown for data 44 representing one or more of the data 44 types—e.g. strain data, ECG data, etc.).

Figure 14B:
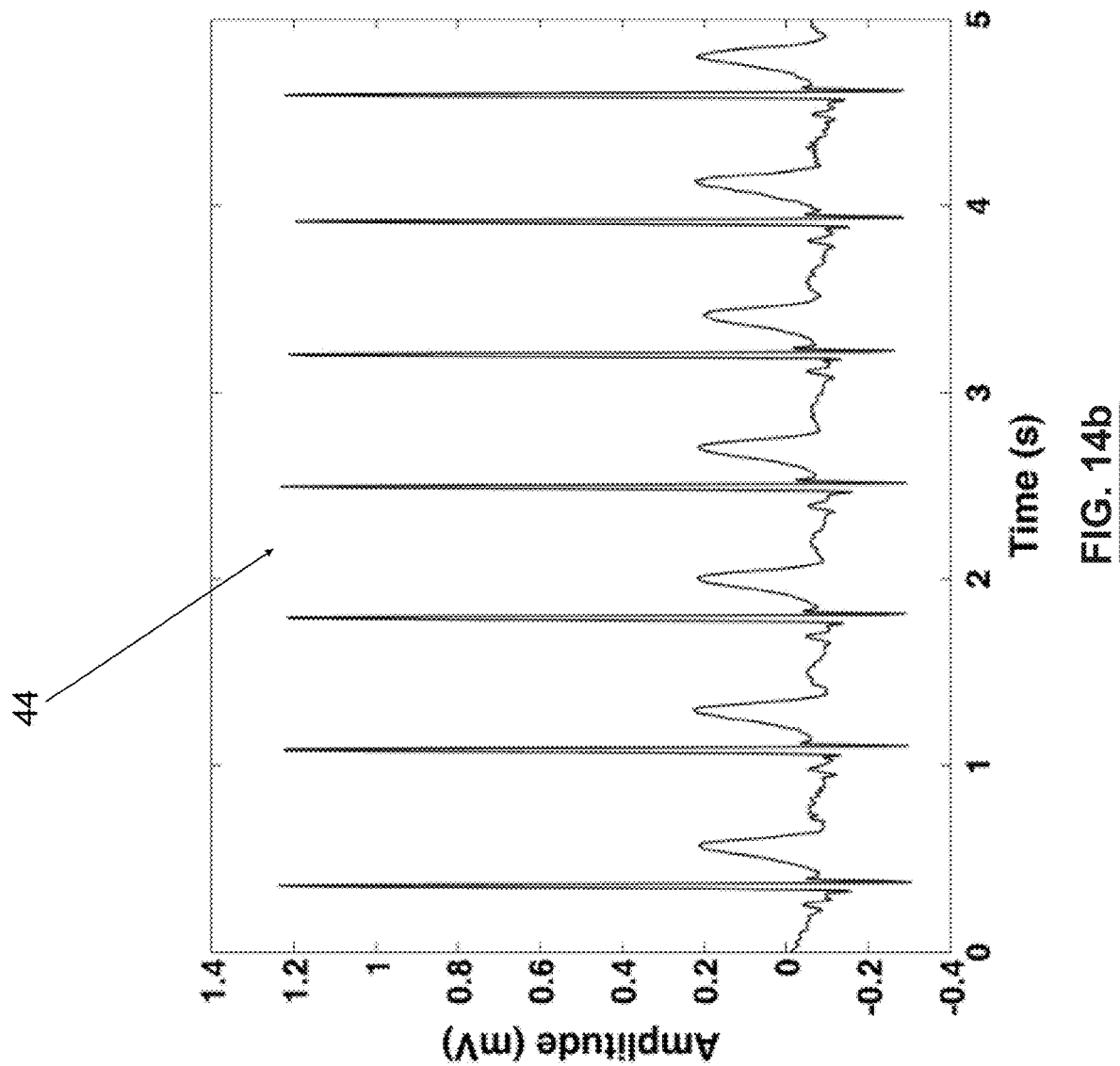
Figure 14C:
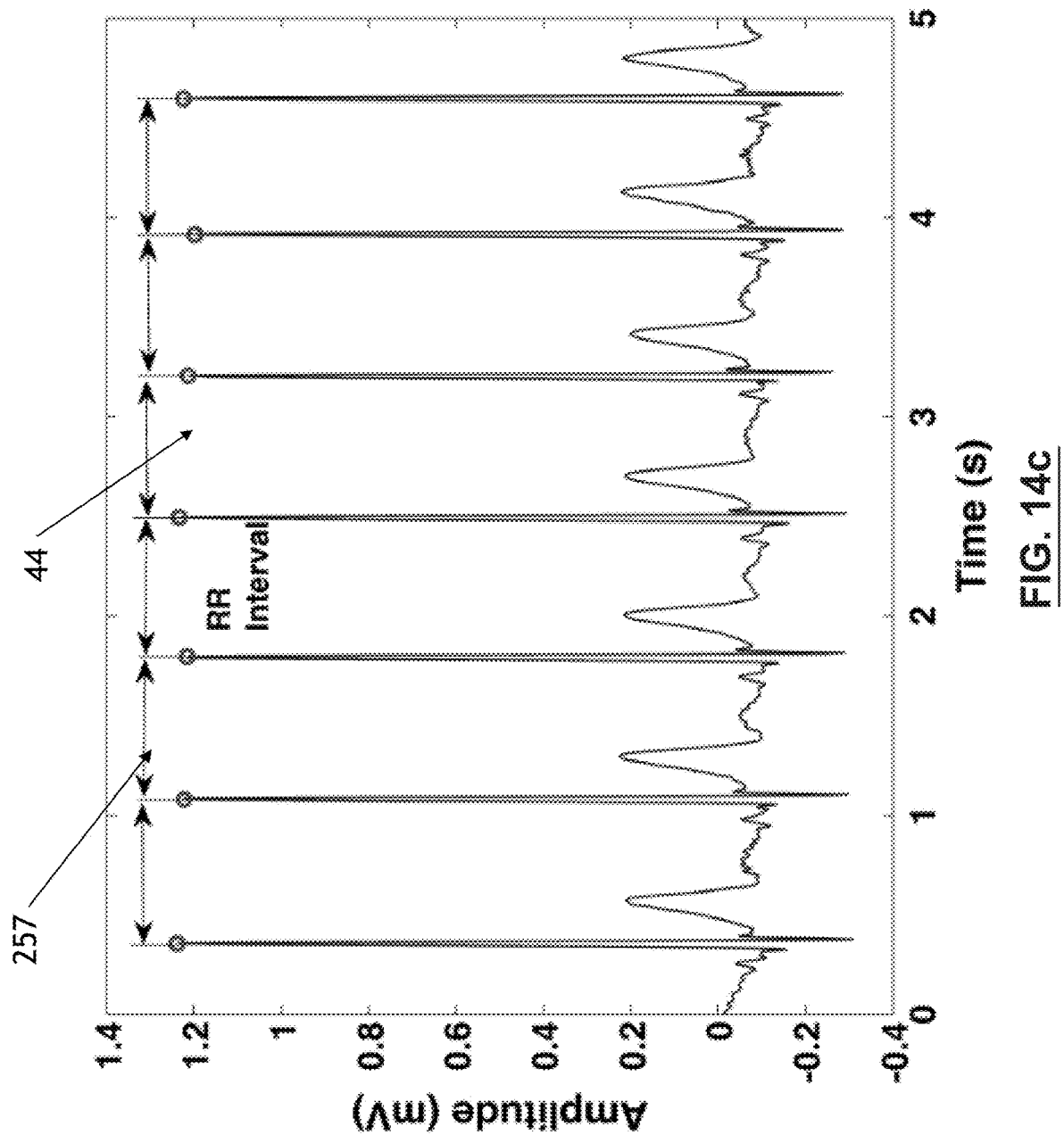
Figure 14D:
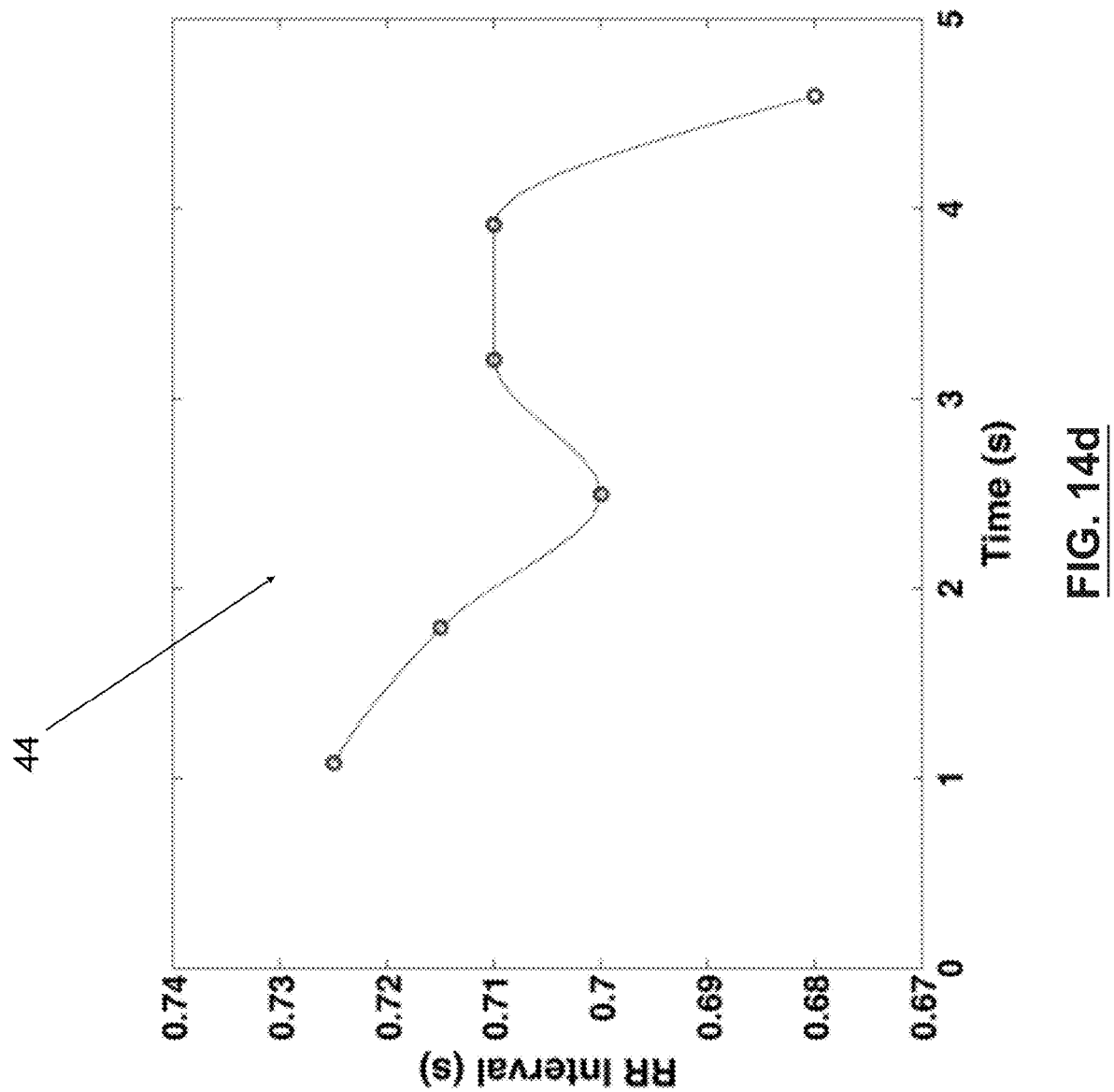
Figure 14E:
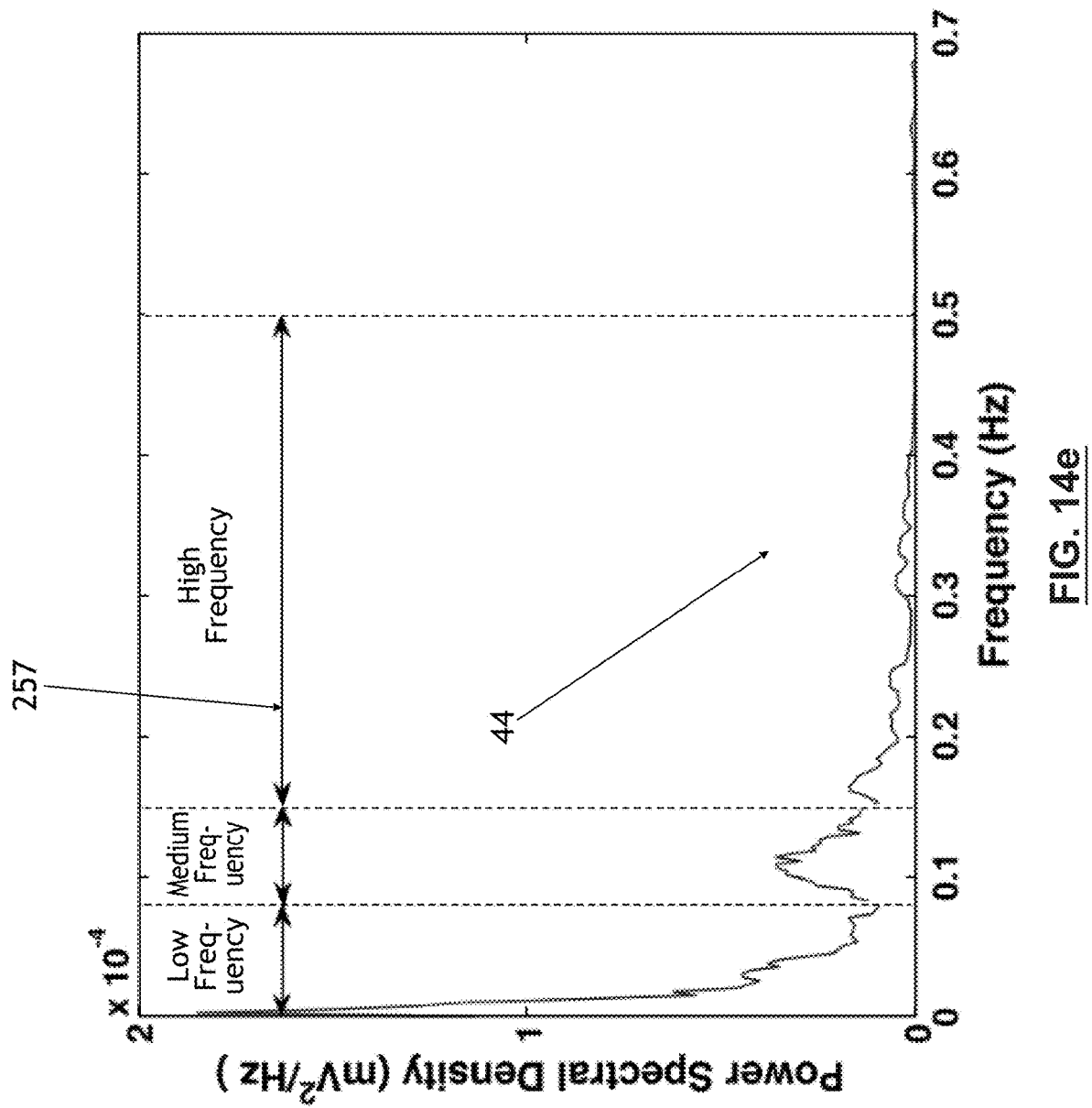
Figure 14F:
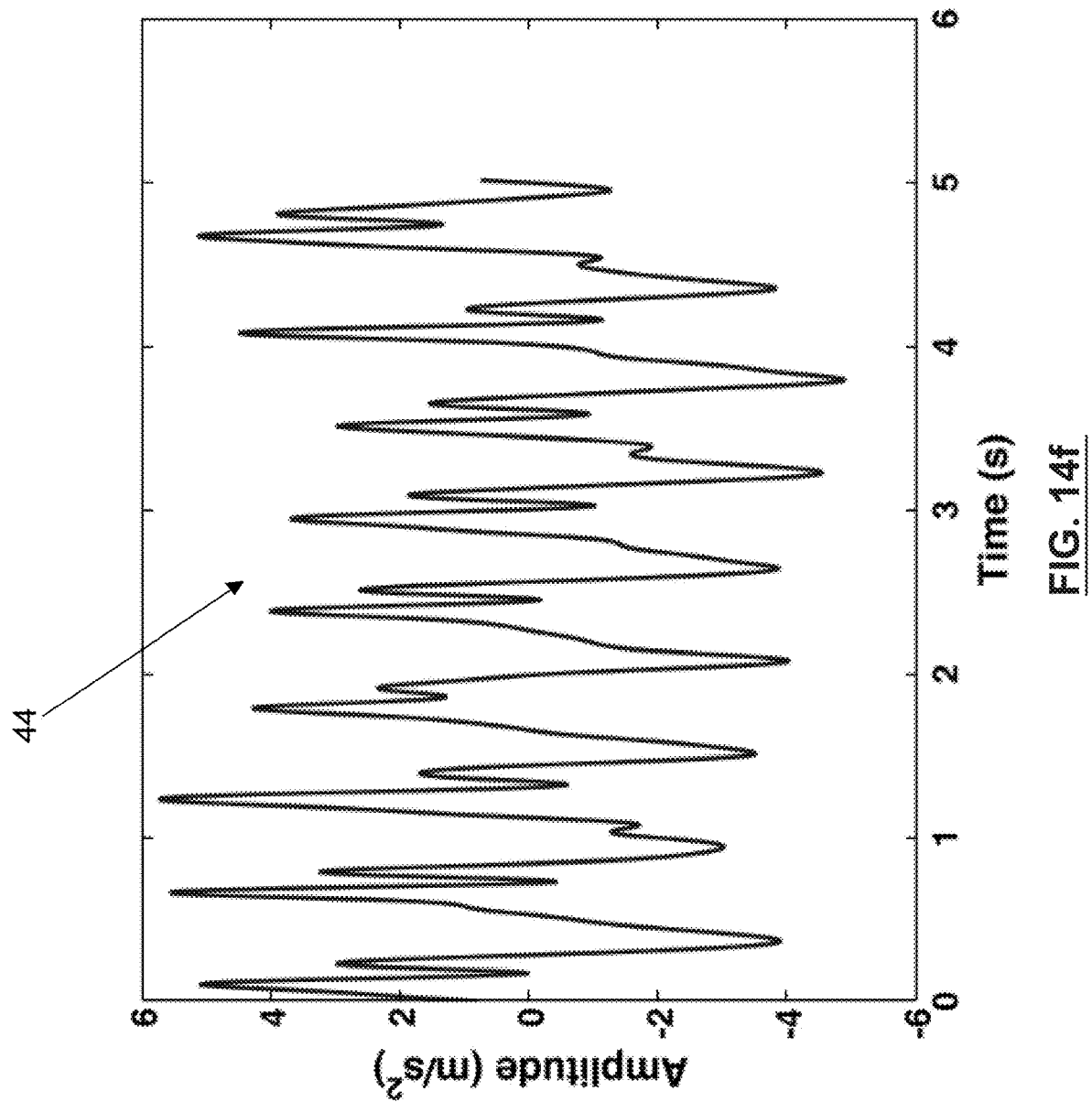
Figure 14G:
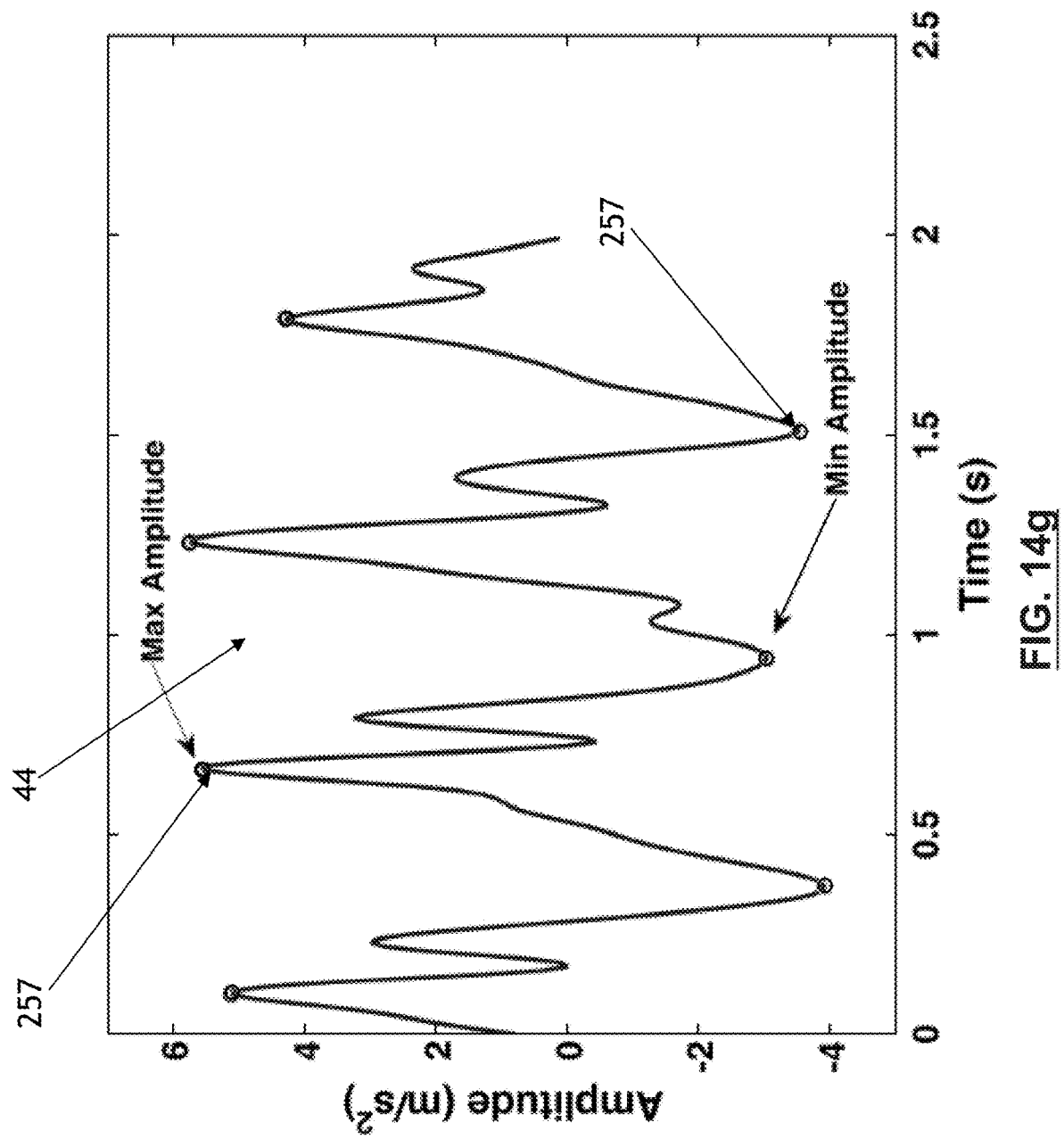
Figure 14I:
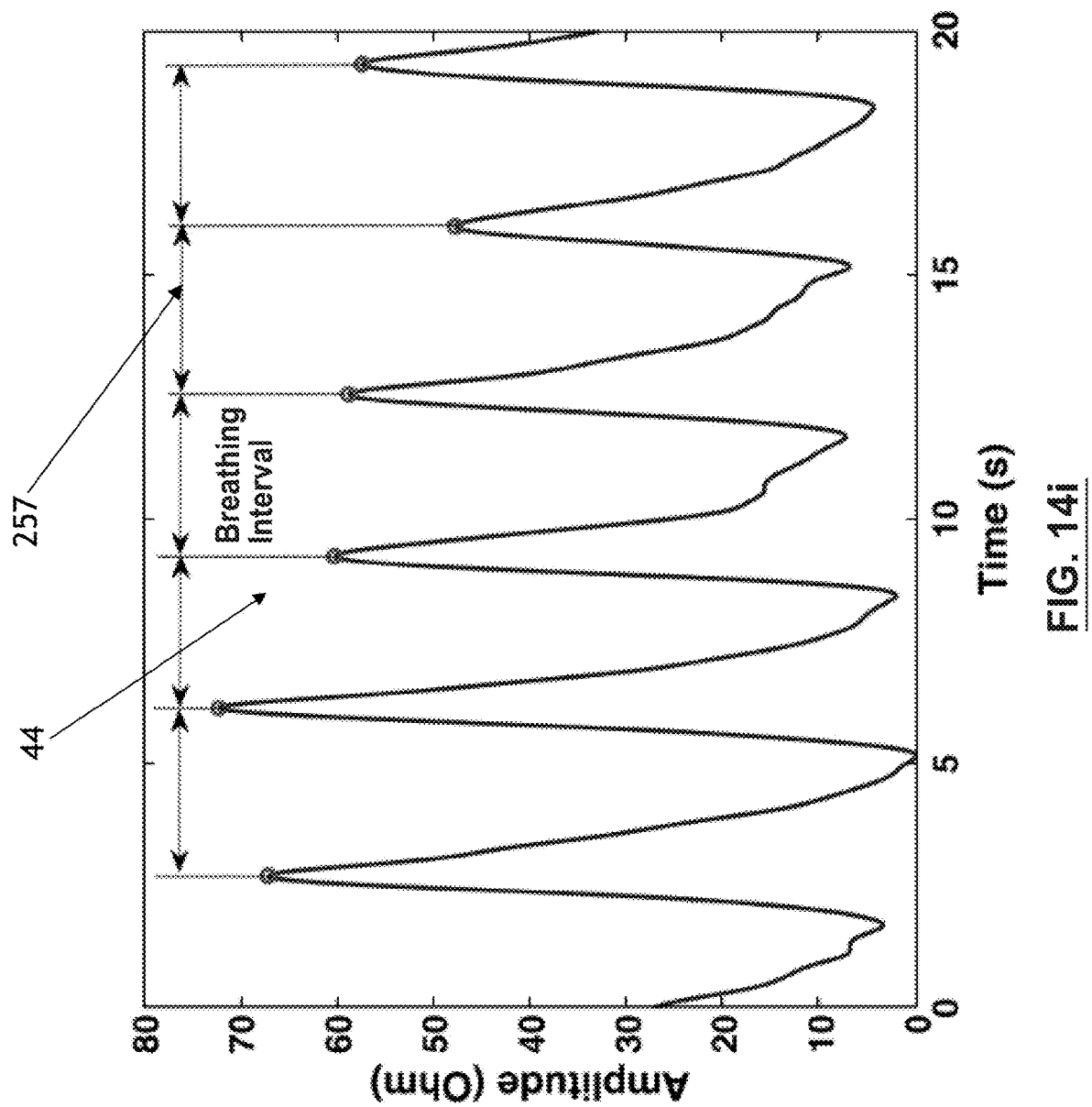
Figure 14J:
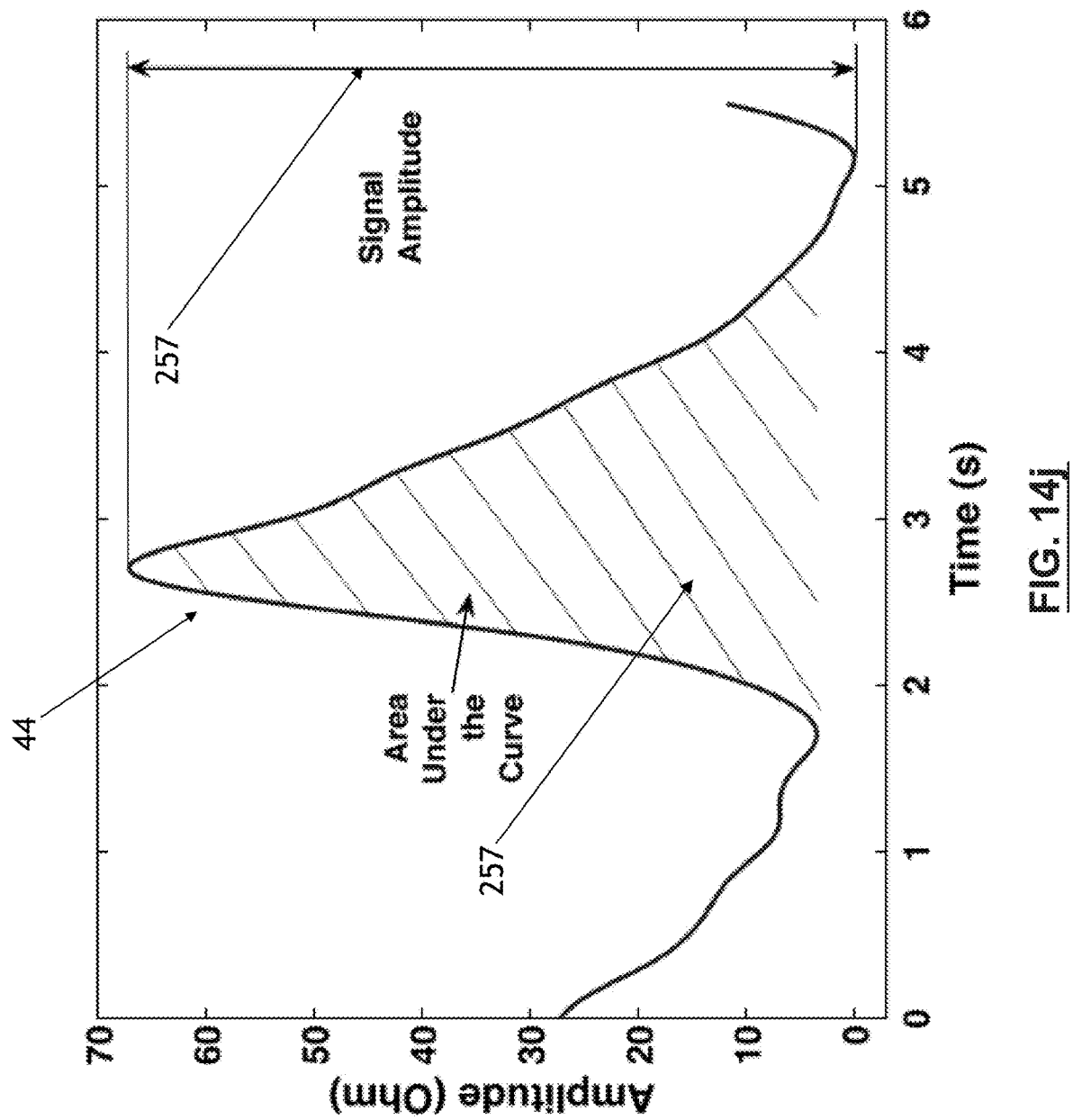
Figure 14K:
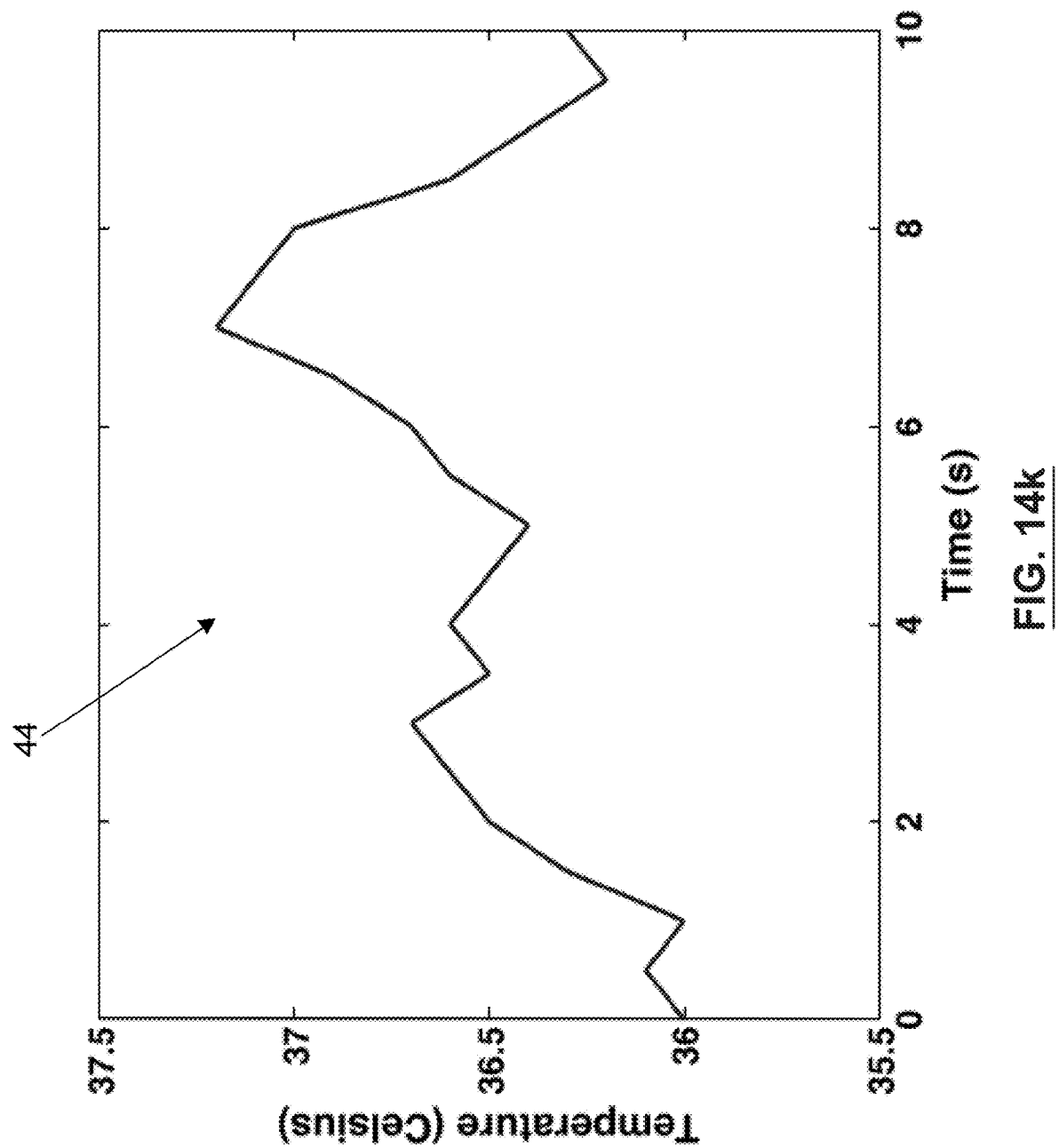

Example data 44 can be such as but not limited to: FIG. 14b of a High-pass Filtered ECG signal 44, FIG. 14c of a RR-interval detection (e.g. feature 257) from filtered ECG signal 44; FIG. 14d of a interpolated RR-interval time series for ECG signal data 44; FIG. 14e showing Power spectrum features 257 from the interpolated RR-interval time series ECG signal data 44; FIG. 14f showing a High-pass Filtered Accelerometer x-axis data 44, while walking; FIG. 14g showing Time domain statistical feature 257 computation from the accelerometer signal data 44; FIG. 14h showing a High-pass filtered respiration signal data 44 obtained from the strain gauge sensor 12; FIG. 14i showing Breathing interval detection features 257 from filtered of the respiration signal data 44; FIG. 14j showing Time domain feature 257 extraction from the filtered respiration signal data 44; FIG. 14k showing Raw temperature signal data 44; and FIG. 14l showing Time domain feature 257 extraction from the temperature signal data 44.

Figure 16:
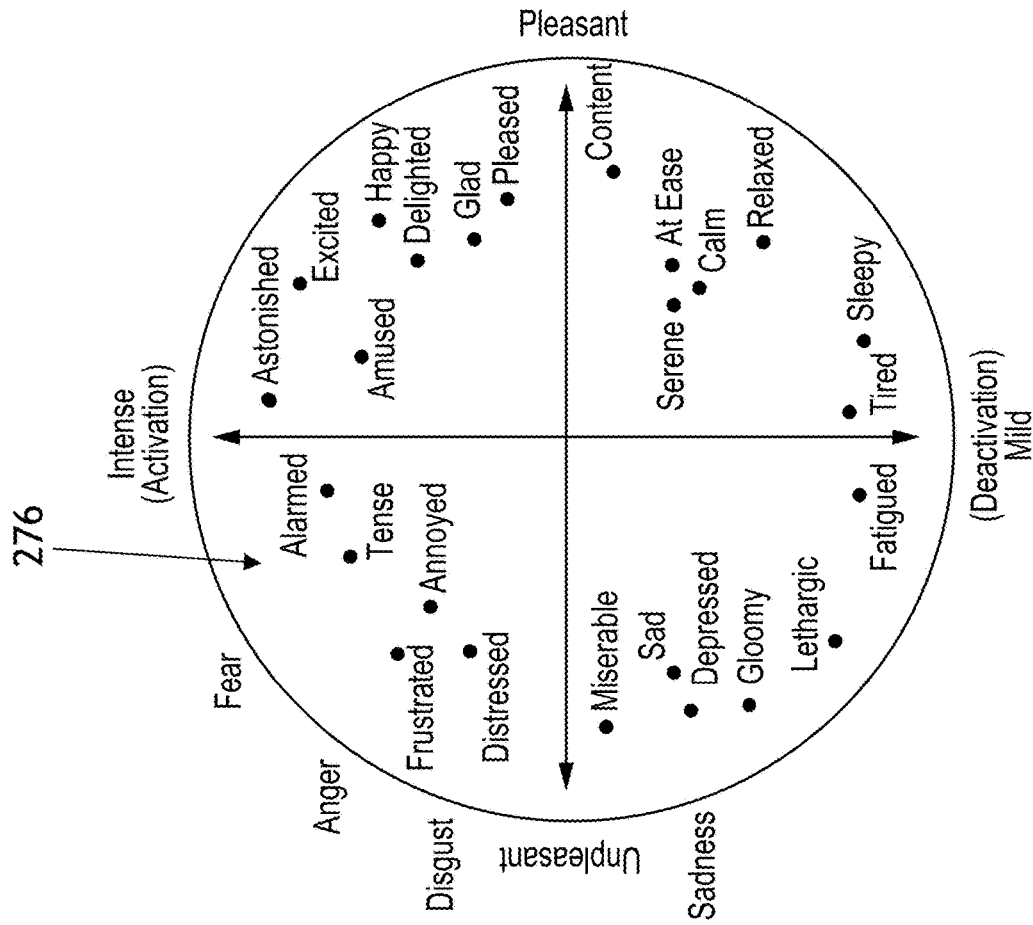
FIG. 16 shows example physiological states of the wearer of FIG. 1.

Referring to FIG. 16, shown is are a plurality of different potential states 276 (e.g. emotional states) of the wearer 8, such that the data model 109 can be configured to correlate one or more of these states via the feature set(s) 260 and relationship(s) pairing between emotional level (e.g. degree of happiness vs. sadness, degree of distressed vs. at ease, degree of tense vs. calm, excited vs. fatigued, etc.). As such, upon real time usage of the data model 109 by the garment application 100, the real time mental state 276 of the wearer 8 can be determined using the methods of 200,250 using comparison of real time data 44 with respect of the data model 109 representing one or more emotional states.

Figure 17:
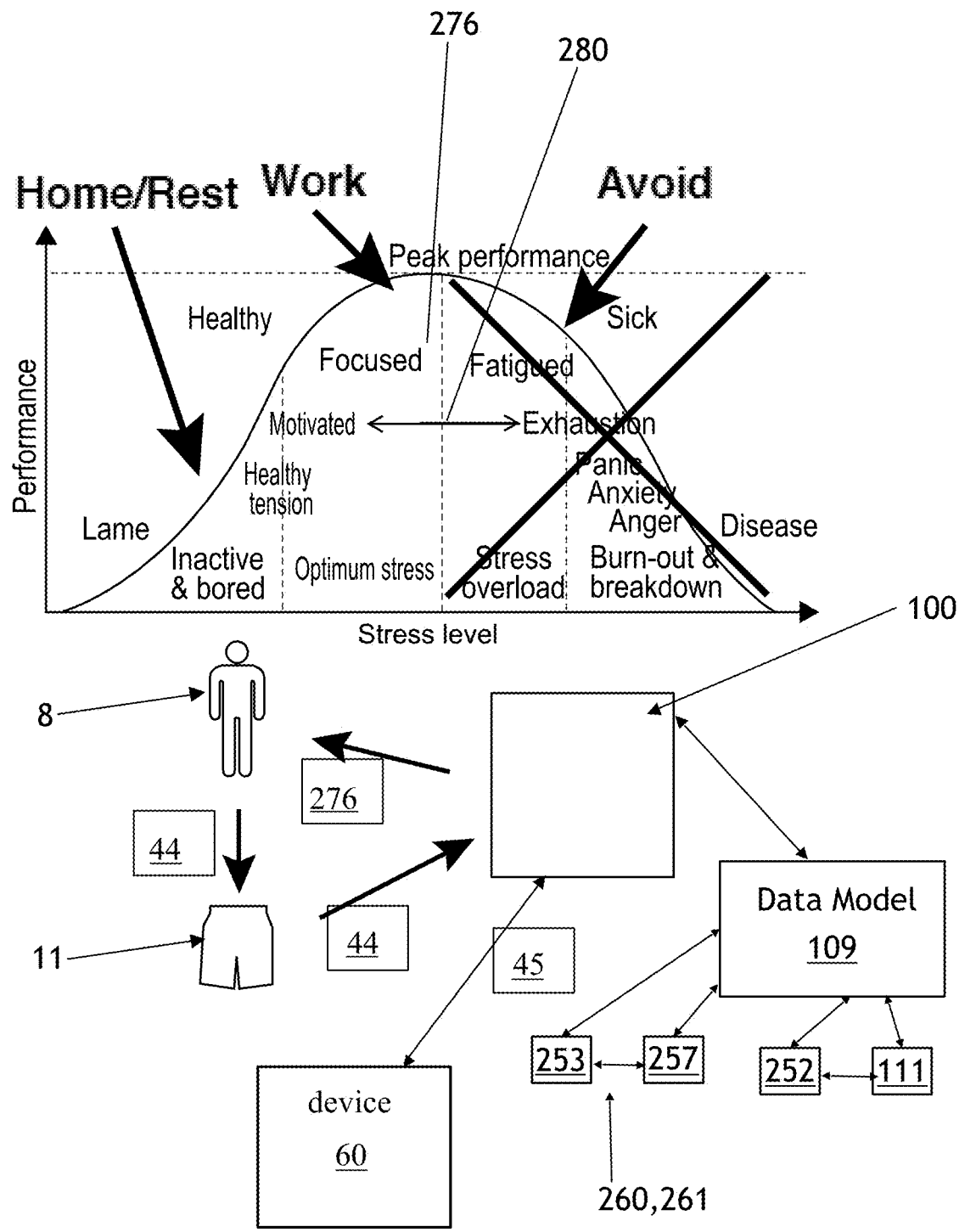
FIG. 17 shows a further embodiment of the system of FIG. 10.
Figure 18A:
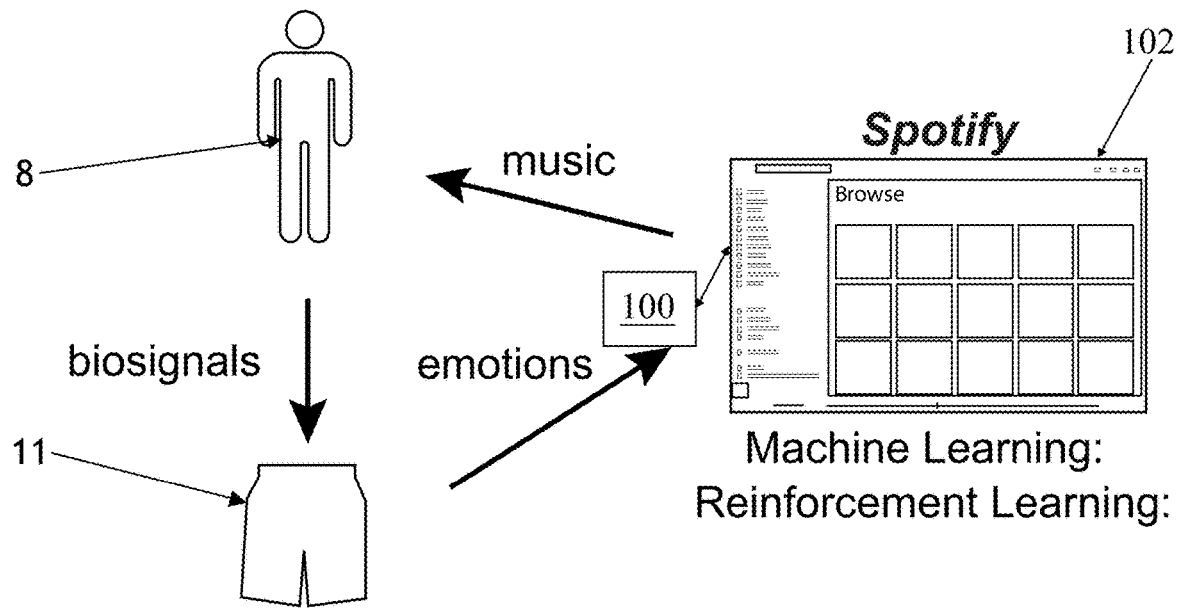
FIGS. 18$a,b$ show further embodiments of the system of FIG. 10.
Figure 18B:
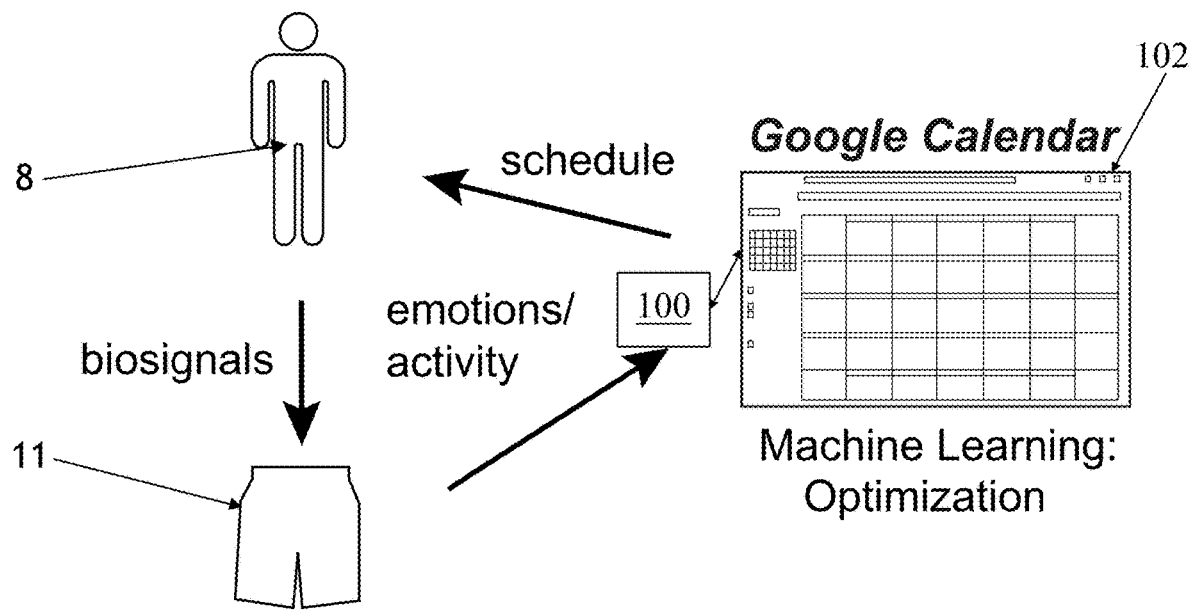

Referring to FIG. 17, shown is an example interaction between the reported states 276 and the collection of data 44 from the garment 11 of the wearer 8 and processing by the garment application 100 via comparison with the data model 109. It is recognized that as discussed above, the reported state(s) 276 can be monitored (see step 210, 212 of FIG. 12) in real time by the garment application 100 and thus changes 280 (e.g. wearer state trending from exhausted 276 to motivated 276) in the reported state 276 can be determined via the garment algorithm 100 in response to the commands 45 (see FIG. 12) generated 206 to the networked device 60. Referring to FIGS. 17 and 18a,b, shown are examples of interaction between the garment application 100 and the device application 102, such that real time responses 45 by the device application 102 (e.g. changes in music type, volume; changes in calendar appointment time, place and content) result from the real time commands 45 generated by the garment application 100 (based on the data 44 and comparison to the data model 109). As discussed above, influence on the reported state 276 can be monitored by the garment application 100 as the wearer 8 goes about their daily routine (e.g. life schedule).

Figure 19:
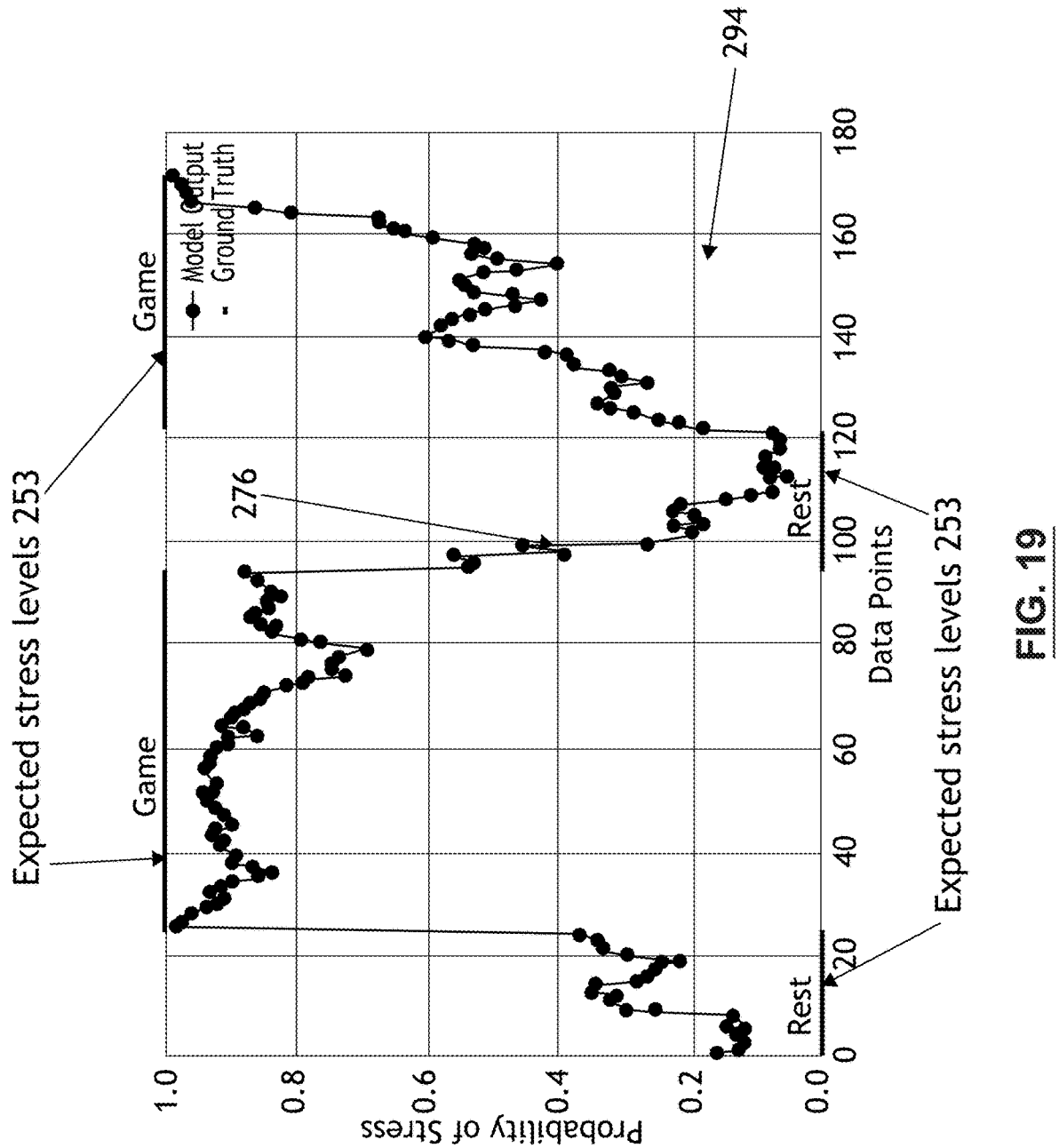
FIG. 19 shows an example feature extraction operation of the system of FIG. 10.

Referring to FIGS. 17 and 19, shown is a graph 294 depicting determined wearer state 276 levels (e.g. stress level) over time (i.e. data points), as the wear 8 played an energetic video game (e.g. environmental stimulus), as compared to the reported emotional state level(s) 253 (e.g. stressed vs relaxed) provided by the wearer 8 (e.g. on a scale of 1-10 what level of emotion the wearer 8 was experiencing) over time while playing the video game.

Figure 20:
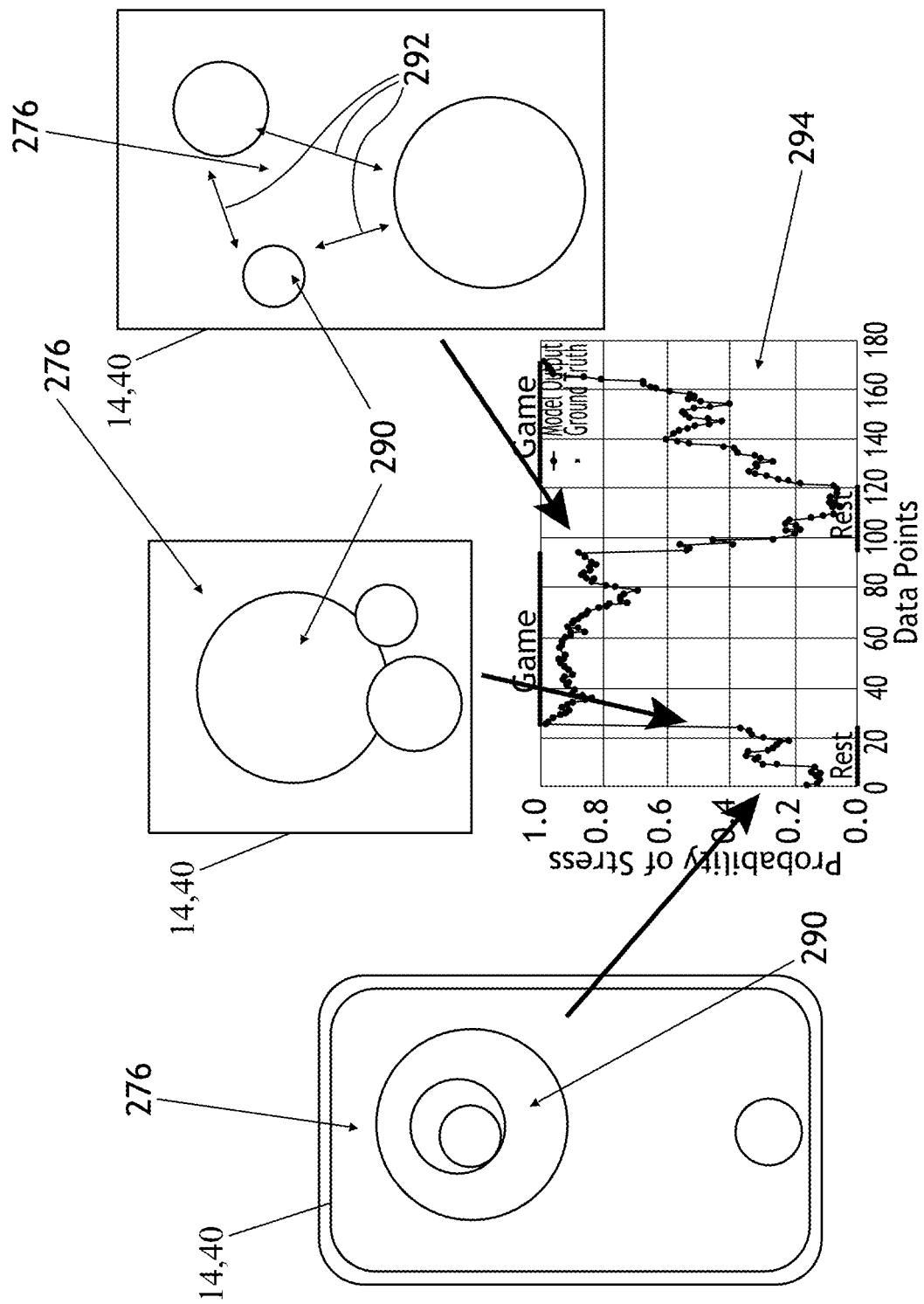
FIG. 20 shows an example graphical representation of the physiological state of the user of FIG. 10.

Referring to FIG. 20, shown are example graphical (e.g. visual) representation of the reported state 276 provided to the device 14,40 for presentation to the wearer 8. The graphical representation consists of a plurality of graphical elements (e.g. spheres) 290, such that their color/shading and spatial distance 292 from one another can be used to represent the degree of monitored emotional state (e.g. stress), as shown on the adjacent graph 294.

Communications Network 22

The user affect (e.g. mental state) analysis and presentation system uses the communications network 22 to facilitate communication between the devices 14,40,41,60 (e.g. device 40,41 hosting the application(s) 100, 250). Preferably, the communications network 22 can be a wide area network such as the Internet, however the network 22 may also comprise one or more local area networks 22. Further, the network 22 need not be a land-based network, but instead may comprise a wireless network and/or a hybrid of a land-based network and a wireless network for enhanced communications flexibility. One example is where the communications network 22 includes a local area network 22 segment (e.g. wired, wireless, etc. on which the network device 14,40,41,60 is registered, communicates on) and a wide area network 22 segment (e.g. the Internet) to which the local area network 22 is connected to. It is also recognized that the garment application 100 and the analysis application 250 can be coupled via the network 22 when on different machines (e.g. a local or wide area network 22 as desired).

Data Processing System 300

Figure 15:
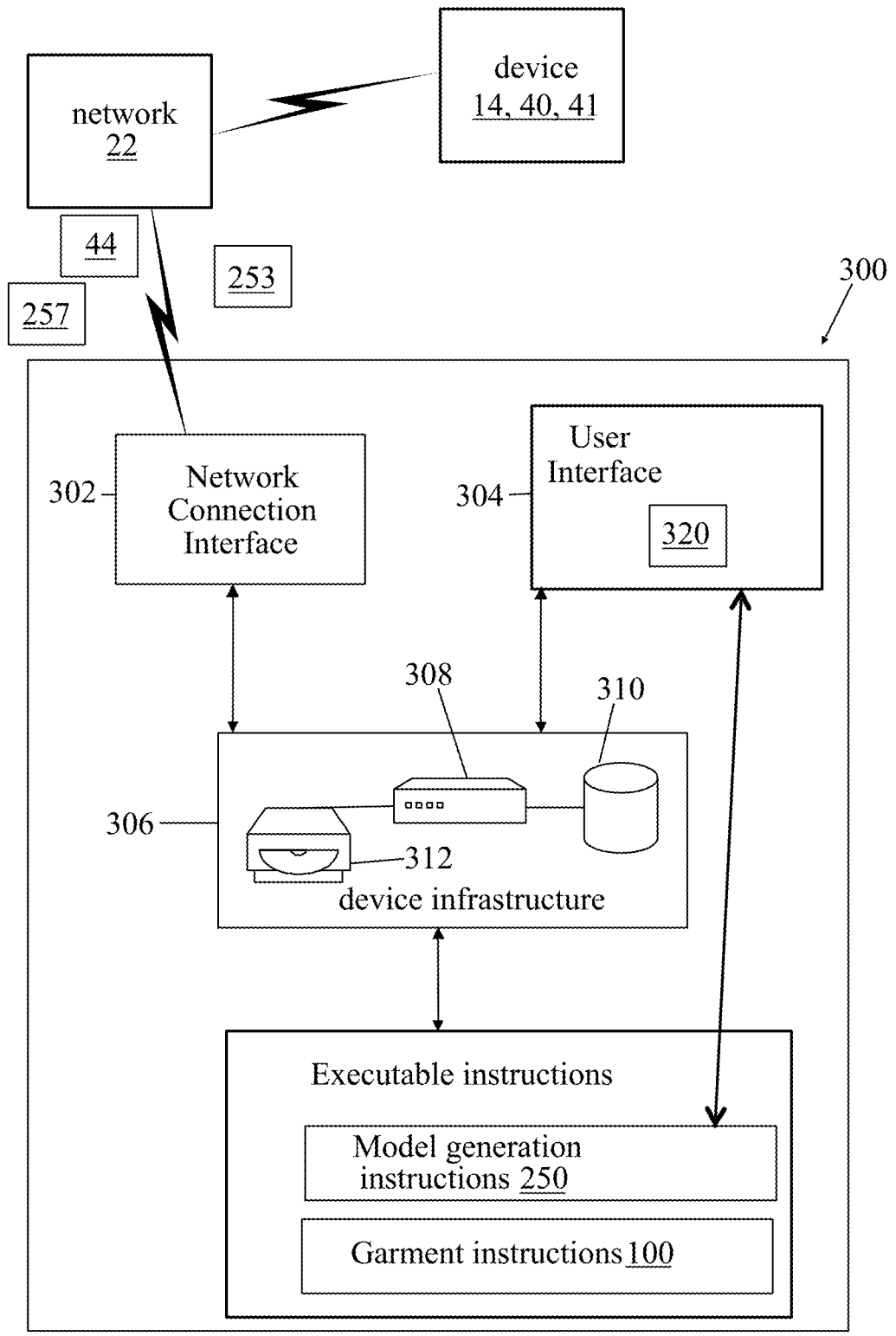
FIG. 15 is a block diagram of a data processing system of the system of FIG. 10.

Referring to FIG. 15, shown is a block diagram of the data processing system 300. It is recognized that the data processing system 300 can be implemented on any one or more of the devices 14,40,41, as desired, as well as providing the reported real time state 276. Each device 14,40,41,60 typically comprises a land-based network-enabled personal computer. However, the invention is not limited for use with personal computers. For instance, one or more of the network devices 14,40,41,60 can comprise a wireless communications device, such as a wireless-enabled personal data assistant, a tablet, or e-mail-enabled mobile telephone if the network 22 is configured to facilitate wireless data communication. The device 14,40,41,60 is capable of supplying the data 44 to the system in order to determine/generate the model(s) 109 as well as to utilize the stored model(s) 109 predict/report real time mental state 276 as described. The user (e.g. wearer 8, system administrator, analyst, etc.) of the device 14,40,41,60 can interact with the data 44 as provided.

As shown in FIG. 15, the data processing system 300 can comprise a network interface 302 coupled to the network 22, the user interface 304 for receipt and presentation (e.g. via text, sound, pictures, video, light and/or haptic feedback) of data 44, reports 276, and the data collection/processing framework 306 in communication with the network interface 302 and the user interface 304. Typically, the network interface 302 comprises an Ethernet network circuit card, however the network interface 302 may also comprise an RF antenna for wireless communication over the communications network 22. Preferably, the user interface 304 comprises a data entry device (such as keyboard, microphone or writing tablet), and a display device (such as a CRT or LCD display). The data processing system 300 includes a central processing unit (CPU) 308, and a non-volatile memory storage device (DISC) 310 (such as a magnetic disc memory or electronic memory) and a read/write memory (RAM) 312 both in communication with the CPU 308. The DISC 310 includes data which, when loaded into the RAM 312, comprise processor instructions for the CPU 308 which define memory objects for allowing the device 14,40,41,60 to operate the applications(s) 100,102,250.

Storage 310 Examples

In view of the above descriptions of storage 310, the storage 310 can be configured as keeping the stored data (e.g. models 109 and related data) in order and the principal (or only) operations on the stored data are the addition of and removal of the stored data from the storage (e.g. FIFO, FIAO, etc.). For example, the storage 310 can be a linear data structure for containing and subsequent accessing of the stored data and/or can be a non-linear data structure for containing and subsequent accessing of the stored data (e.g. models 109, associated model data such as features 257, effects 253, etc., data 44, applications 100,102,250, etc.). Further, the storage 310 receives various entities such as applicable data/instructions that are stored and held to be processed later. In these contexts, the storage 310 can perform the function of a buffer, which is a region of memory used to temporarily hold data while it is being moved from one place to another. Typically, the data is stored in the memory when moving the data between processes within/between one or more computers. It is recognized that the storage 310 can be implemented in hardware, software, or a combination thereof. The storage 310 is used in the system when there is a difference between the rate/time at which data is received and the rate/time at which the data can be processed.

Further, it will be understood by a person skilled in the art that the memory/storage 310 described herein is the place where data can be held in an electromagnetic or optical form for access by the computer processors/modules 14,40,41,60. There can be general usages: first, memory is frequently used to mean the devices and data connected to the computer through input/output operations such as hard disk and tape systems and other forms of storage not including computer memory and other in-computer storage. Second, in a more formal usage, memory/storage has been divided into: (1) primary storage, which holds data in memory (sometimes called random access memory or RAM) and other "built-in" devices such as the processor's L1 cache, and (2) secondary storage, which holds data on hard disks, tapes, and other devices using input/output operations. Primary storage can be faster to access than secondary storage because of the proximity of the storage to the processor or because of the nature of the storage devices. On the other hand, secondary storage can hold much more data than primary storage. In addition to RAM, primary storage includes read-only memory (ROM) and L1 and L2 cache memory. In addition to hard disks, secondary storage includes a range of device types and technologies, including diskettes, Zip drives, redundant array of independent disks (RAID) systems, and holographic storage. Devices that hold storage are collectively known as storage media.

A database is one embodiment of memory 310 as a collection of information that is organized so that it can easily be accessed, managed, and updated. In one view, databases can be classified according to types of content: bibliographic, full-text, numeric, and images. In computing, databases are sometimes classified according to their organizational approach. The most prevalent approach is the relational database, a tabular database in which data is defined so that it can be reorganized and accessed in a number of different ways. A distributed database is one that can be dispersed or replicated among different points in a network. An object-oriented programming database is one that is congruent with the data defined in object classes and subclasses. Computer databases typically contain aggregations of data records or files. Typically, a database manager provides users the capabilities of controlling read/write access, specifying report generation, and analyzing usage. Databases and database managers are prevalent in large mainframe systems, but are also present in smaller distributed workstation and mid-range systems such as the AS/400 and on personal computers. SQL (Structured Query Language) is a standard language for making interactive queries from and updating a database such as IBM's DB2, Microsoft's Access, and database products from Oracle, Sybase, and Computer Associates.

Memory/storage can also be defined as an electronic holding place for instructions and data that the computer's microprocessor can reach quickly. When the computer is in normal operation, its memory usually contains the main parts of the operating system and some or all of the application programs and related data that are being used. Memory is often used as a shorter synonym for random access memory (RAM). This kind of memory is located on one or more microchips that are physically close to the microprocessor in the computer.

In terms of a server, it is recognized that the device 40,41,60 as host for the application(s) 100,102,250 can be configured as hardware, software, or typically a combination of both hardware and software to provide a network entity that operates as a socket listener via the network 22. It is recognized that any computerized process that shares a resource (e.g. data) to one or more client processes can be classified as a server in the network system. The term server can also be generalized to describe a host that is deployed to execute one or more such programs, such that the host can be one or more configured computers that link other computers or electronic devices together via the network 22. The server(s) can provide specialized services across the network 22, for example to private users inside a large organization or to public users via the Internet 22. In the network system, the servers can have dedicated functionality and/or can share functionality as described. Enterprise servers are servers that are used in a business context and can be run on/by any capable computer hardware. In the hardware sense, the word server typically designates computer models intended for running software applications under the heavy demand of a network 22 environment. In this client-server configuration one or more machines, either a computer or a computer appliance, share information with each other with one acting as a host for the other. While nearly any personal computer is capable of acting as a network server, a dedicated server will contain features making it more suitable for production environments. These features may include a faster CPU, increased high-performance RAM, and typically more than one large hard drive. More obvious distinctions include marked redundancy in power supplies, network connections, and even the servers themselves.

We claim:

1. A computer implemented method of using a sensor platform of a garment of a wearer in order to determine a wearer state using a plurality of sensed biometric data, the method comprising a set of stored instructions for execution by a computer processor for:
    receiving from sensors of the sensor platform a plurality of biometric data, wherein the sensor platform is incorporated into an article of clothing worn by the wearer having a plurality of different sensor types, and wherein the sensor platform and a computing device coupled to said sensor platform are positioned at a waist of the wearer and wherein at least one of said sensors is positioned at one or more locations on the waist of the wearer, and wherein said sensors include a strain gauge sensor and a gyroscope;
    receiving, from the wearer, user affect levels corresponding to a mental state of the wearer;
    extracting a plurality of data features from the plurality of biometric data and the user affect levels based on combining a plurality of sensor readings from the sensors and the user affect levels in time and/or frequency domain windows, the plurality of sensor readings including the plurality of different sensor types, wherein processing data received from said strain gauge sensor and said gyroscope provides a determination of a posture of the wearer as one of the plurality of data features, the posture indicating a degree of bending at the waist of the wearer, wherein said processing said data received from said strain gauge sensor and said gyroscope includes differentiating a degree of strain contributing to said posture, and discounting a degree of said plurality of biometric data from said gyroscope on a calculation of said determination of said posture based on said degree of bending at said waist of said wearer being due to a body composition of said wearer;
    creating a data model by applying one or more machine learning methods to determine relationships between said plurality of data features and the user affect levels;
    receiving a plurality of current biometric data from the sensor platform;
    wherein a device account registered with a device application of the computing device contains wearer settings information and device operation settings, wherein the wearer settings information defines the wearer's environment based on said computing device being paired with an adjacent device;
    determining a current wearer state based on the wearer's environment and on extracting a plurality of current data features including a current posture from said current biometric data and matching said plurality of current data features with a set of representative feature-affect pairings of the data model, the feature-affect pairings including effects representing possible states for the wearer, the data model including a data pattern indicative of the wearer state based on a combination of the plurality of sensor readings including the posture indicating a current degree of bending at the waist of the wearer, wherein said matching comprises comparing the plurality of current data features to a threshold of the data model pertaining to the combination including the posture as sensed by one or more of the sensors, said current wearer state including a current mental state of said wearer; and
    reporting the current wearer state to the wearer as a presentation using a user interface of a presentation device.

2. The method of claim 1, wherein the presentation device is a computing device coupled to the garment.

3. The method of claim 1, wherein the presentation device is a remote computing device coupled to a computing device of the garment.

4. The method of claim 1 further comprising the placement of at least some of the sensors of the sensor platform being positioned in one or more body regions on the waist of the wearer where muscle noise is inhibited.

5. The method of claim 4, wherein the one or more body regions include a region selected from the group consisting of: adjacent to a hip; and adjacent to a kidney.

6. The method of claim 4 further comprising a sensor pair of the sensors positioned on either side of a centerline of a band of the article of clothing, the band positioning the sensor platform adjacent of the waist of the wearer.

7. The method of claim 6, wherein the centerline is oriented front to back of the wearer rather than oriented side to side of the wearer.

8. The method of claim 1 further comprising generating a command based on the current wearer state and sending the command over a communications network to a networked device in order to effect a change in an operational behaviour of the networked device.

9. The method of claim 8, wherein the wearer has the device account with the networked device, the device account administered with an interaction service in communication with the networked device over the communications network.

10. The method of claim 8, wherein the device operation settings are applicable to permitted functionality of the networked device accessible by the command.

11. The method of claim 10, wherein the wearer settings information includes a location setting specifying the physical location of the networked device, wherein the physical location is determined based on the sensor platform being communicatively paired with the networked device.

12. The method of claim 1, wherein the data model includes at least one of a physical location, a time of day or an activity reading in order to determine the wearer state.

13. The method of claim 1, wherein the data model includes at least one of a physical location or a time of day in order to determine the wearer state.

14. The method of claim 1, wherein said adjacent device is a vehicle.

15. The method of claim 1, wherein said adjacent device is an exercise equipment device.

* * * * *